Figure 1:
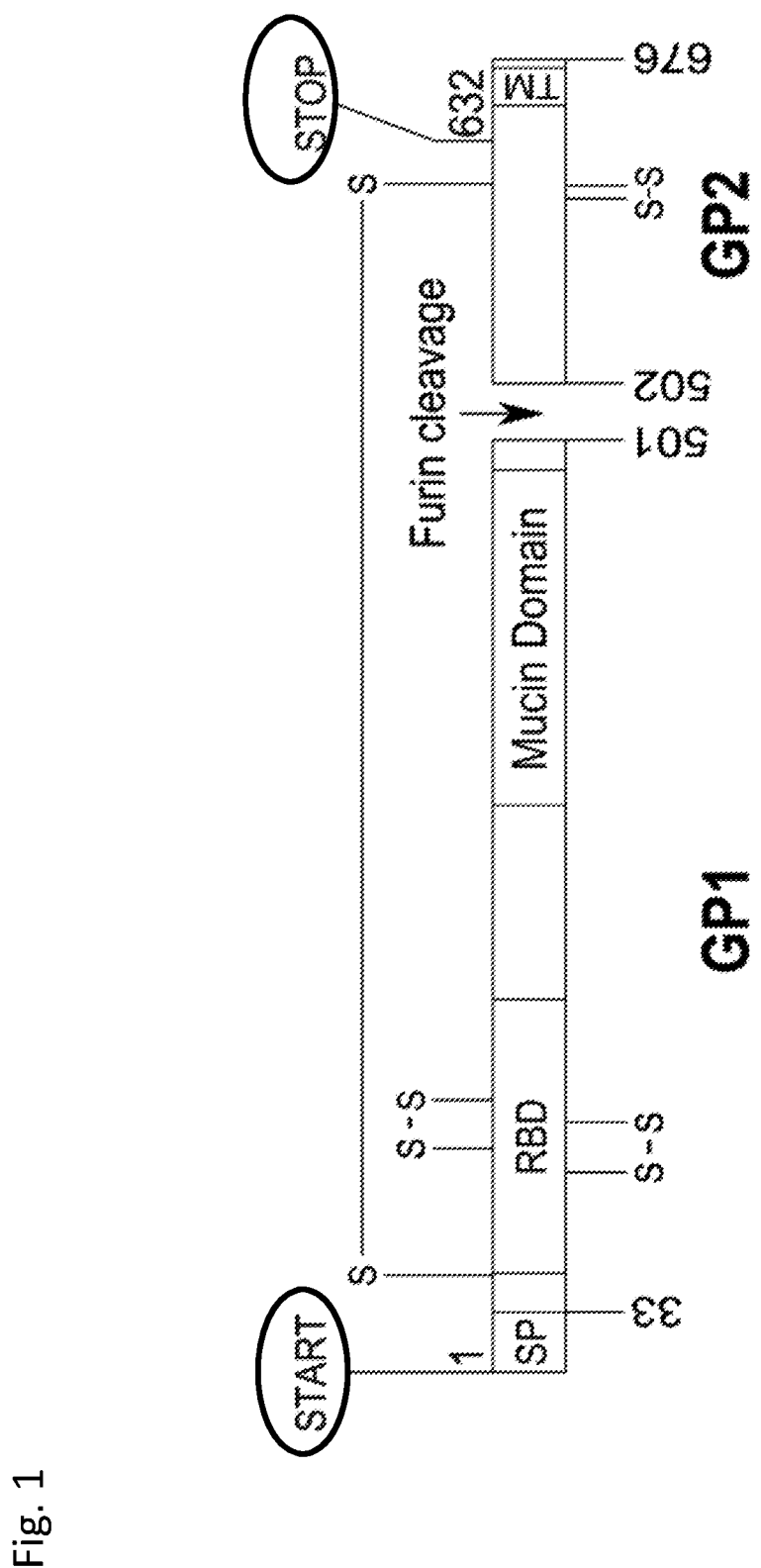

US010519219B2

(12) United States Patent
Carroll et al.

(10) Patent No.: US 10,519,219 B2
(45) Date of Patent: Dec. 31, 2019

(54) FILOVIRUS THERAPY

(71) Applicants: The Secretary of State for Health, London (GB); MicroPharm Limited, Newcastle, Emlyn (GB); The Chancellor, Masters and Scholars of the University of Oxford, Oxford, Oxfordshire (GB)

(72) Inventors: Miles Carroll, Salisbury (GB); Stuart Dowall, Salisbury (GB); Roger Hewson, Salisbury (GB); Ian Cameron, Newcastle (GB); John Landon, Newcastle (GB); Antra Zeltina, Oxford (GB); David Stuart, Oxford (GB); Thomas Bowden, Oxford (GB)

(73) Assignees: The Secretary of State for Health, London (GB); MicroPharm Limited, Newcastle, Emlyn (GB); The Chancellor, Masters and Scholars of the University of Oxford, Oxford, Oxfordshire (GB)

( * ) Notice: Subject to any disclaimer, the term of this patent is extended or adjusted under 35 U.S.C. 154(b) by 0 days.

(21) Appl. No.: 15/549,933

(22) PCT Filed: Feb. 10, 2016

(86) PCT No.: PCT/GB2016/050321
§ 371 (c)(1),
(2) Date: Aug. 9, 2017

(87) PCT Pub. No.: WO2016/128748
PCT Pub. Date: Aug. 18, 2016

(65) Prior Publication Data

US 2018/0105580 A1 Apr. 19, 2018

(30) Foreign Application Priority Data

Feb. 10, 2015 (GB) .................................. 1502209.8

(51) Int. Cl.

| | |
|---|---|
| *C07K 16/10* | (2006.01) |
| *A61K 39/42* | (2006.01) |
| *A61K 39/12* | (2006.01) |
| *A61K 45/06* | (2006.01) |
| *A61K 39/00* | (2006.01) |

(52) U.S. Cl.
CPC .............. *C07K 16/10* (2013.01); *A61K 39/12* (2013.01); *A61K 39/42* (2013.01); *A61K 45/06* (2013.01); *A61K 2039/505* (2013.01); *C07K 2317/10* (2013.01); *C07K 2317/20* (2013.01); *C07K 2317/34* (2013.01); *C07K 2317/76* (2013.01); *C12N 2760/14011* (2013.01); *C12N 2760/14134* (2013.01); *C12N 2760/14211* (2013.01)

(58) Field of Classification Search
None
See application file for complete search history.

(56) References Cited

FOREIGN PATENT DOCUMENTS

| | | | |
|---|---|---|---|
| RU | 2 089 217 | C1 | 9/1997 |
| RU | 2 257 916 | C1 | 8/2005 |
| WO | 01/016183 | A1 | 3/2001 |
| WO | 2004/018649 | A2 | 3/2004 |
| WO | 2006/037038 | A1 | 4/2006 |
| WO | 2009/094755 | A1 | 8/2009 |
| WO | 2011/071574 | A2 | 6/2011 |
| WO | 2015/127136 | A2 | 8/2015 |

OTHER PUBLICATIONS

Kudoyarova-Zubavichene et al. Preparation and Use of Hyperimmune Serum for Prophylaxis and Therapy of Ebola Virus Infections. The Journal of Infectious Diseases 1999;179(Suppl 1):S218-23. Submitted in IDS filed on Dec. 18, 2017.*
Smith et al. Interferon-β Therapy Prolongs Survival in Rhesus Macaque Models of Ebola and Marburg Hemorrhagic Fever. The Journal of Infectious Diseases 2013;208:310-8.*
Qiu et al. Successful Treatment of Ebola Virus—Infected Cynomolgus Macaques with Monoclonal Antibodies. Science Translational Medicine Jun. 13, 2012; 4(138): 138ra81.*
Konduru et al. Ebola virus glycoprotein Fc fusion protein confers protection against lethal challenge in vaccinated mice. Vaccine 29 (2011) 2968-2977.*
Leenaars, et al. Critical Steps in the Production of Polyclonal and Monoclonal Antibodies: Evaluation and Recommendations. ILAR Journal, vol. 46, Issue 3, Jan. 1, 2005, pp. 269-279.*
Jahrling et al. Ebola hemorrhagic fever: Evaluation of passive immunotherapy in nonhuman primates. J. Infect. Dis. 196 (Suppl. 2), S400-S403 (2007).*
Jahrling et al. Evaluation of immune globulin and recombinant interferon-a2b for treatment of experimental Ebola virus infections. J. Infect. Dis. 179 (Suppl. 1), S224-S234 (1999).*
Jahrling et al. Passive immunization of Ebola virus-infected cynomolgus monkeys with immunoglobulin from hyperimmune horses. Arch. Virol. Suppl. 11, 135-140 (1996).*
Janeway et al. Immunobiology: The Immune System in Health and Disease. 5th edition. New York: Garland Science; 2001. B-cell activation by armed helper T cells. Available from: https://www.ncbi.nlm.nih.gov/books/NBK27142/.*
Dowall, S.D., et al., "Development of a Cost-Effective Ovine Polyclonal Antibody-Based Product, EBOTAb, to Treat Ebola Virus Infection," Journal of Infectious Diseases 213(7):1124-1133, Apr. 2016.
Kudoyarova-Zubavichene, N.M., et al., "Preparation and Use of Hyperimmune Serum for Prophylaxis and Therapy of Ebola Virus Infections," Journal of Infectious Diseases 179 (Suppl 1):S218-S223, Feb. 1999.

(Continued)

*Primary Examiner* — Nianxiang Zou
(74) *Attorney, Agent, or Firm* — Christensen O'Connor Johnson Kindness PLLC

(57) ABSTRACT

The present invention provides antibodies, for use in the treatment, suppression prevention of Filovirus disease, particularly Ebola virus disease. Also provided immunogens for use in eliciting such antibodies.

19 Claims, 18 Drawing Sheets

Specification includes a Sequence Listing.

(56) References Cited

OTHER PUBLICATIONS

Kuhn, J.H., et al., "Proposal for a Revised Taxonomy of the Family Filoviridae: Classification, Names of Taxa and Viruses, and Virus Abbreviations," Archives of Virology 155(12):2083-2103, Dec. 2010.

Martin, J.E., et al., "A DNA Vaccine for Ebola Virus is Safe and Immunogenic in a Phase I Clinical Trial," Clinical and Vaccine Immunology 13(11):1267-1277, Nov. 2006.

MicroPharm Limited, "Ovine Antibodies to Treat Ebola Virus Disease," Jan. 14, 2015, <http://www.micropharm.co.uk/news/2015/1/ovine_antibodies_to_treat_ebola> [retrieved Jul. 14, 2016], 4 pages.

Nakayama, E., et al., "Antibody-Dependent Enhancement of Marburg Virus Infection," Journal of Infectious Diseases 204 (Suppl 3):S978-S985, Nov. 2011.

Oswald, W.B., et al., "Neutralizing Antibody Fails to Impact the Course of Ebola Virus Infection in Monkeys," PLoS Pathogens 3(1):0062-0066, Jan. 2007.

Sarwar, U.N., et al., "Safety and Immunogenicity of DNA Vaccines Encoding Ebolavirus and Marburgvirus Wild-Type Glycoproteins in a Phase I Clinical Trial," Journal of Infectious Diseases 211(4):549-557, Feb. 2015.

Sullivan, N.J., et al., "Immune Protection of Nonhuman Primates Against Ebola Virus With Single Low-Dose Adenovirus Vectors Encoding Modified GPs," PLoS Medicine 3(6):0865-0873, Jun. 2006.

Search Report Under Section 17(5), dated Oct. 30, 2015, issued in Application No. GB1502209.8, filed Feb. 10, 2015, 5 pages.

Invitation to Pay Additional Fees and, Where Applicable, Protest Fee, dated Apr. 29, 2016, issued in corresponding International Application No. PCT/GB2016/050321, filed Feb. 10, 2016, 7 pages.

International Search Report and Written Opinion, dated Jul. 8, 2016, issued in corresponding International Application No. PCT/GB2016/050321, filed Feb. 10, 2016, 17 pages.

Second Written Opinion of the International Preliminary Examining Authority dated Feb. 8, 2017, issued in corresponding International Application No. PCT/GB2016/050321, filed Feb. 10, 2016, 5 pages.

International Preliminary Report on Patentability, dated May 31, 2017, issued in corresponding International Application No. PCT/GB2016/050321, filed Feb. 10, 2016, 16 pages.

\* cited by examiner

Fig. 2

ELISA: 50% Binding titres of Pooled Whole Ovine Anti-Ebola Virus Glycoprotein (EBOV GPC) Serum, sampled at time points 6, 10 & 14 weeks post-primary immunisation.

FILOVIRUS THERAPY

STATEMENT REGARDING SEQUENCE LISTING

The sequence listing associated with this application is provided in text format in lieu of a paper copy and is hereby incorporated by reference into the specification. The name of the text file containing the sequence listing is 64181_Sequence_listing_file_ST25.txt. The text file is 19.2 KB; was created on Jul. 28, 2017, and is being submitted via EFS-Web with the filing of the specification.

The present invention relates to compositions for use in treating or suppressing Filovirus disease, particularly Ebola virus disease. The present invention also relates to prophylactic uses of said compositions. The present invention also relates to immunogen for use in raising therapeutic antibodies, and methods for producing said immunogen.

Filoviruses belong to a virus family called Filoviridae and can cause severe hemorrhagic fever in humans and nonhuman primates. Filoviruses are filamentous, enveloped particles with a negative-sense, single-stranded RNA genome, approximately 19 kb long. Filovirus genomes are arranged linearly, and contain seven genes in the order 3'-UTR-nucleoprotein (NP)-virion protein (VP)35-VP40-surface glycoprotein (GP)-VP3O-VP24-RNA-dependent RNA polymerase (L)-5'-UTR. The combination and action of the EBOV gene products and their interactions with the host cell contribute to the severe haemorrhagic fever. There are several properties of the polymerase complex that contribute to virulence.

The EBOV GP gene encodes the nonstructural soluble glycoprotein (sGP) but also produces the transmembrane glycoprotein ($GP_{1,2}$) and the small soluble glycoprotein (ssGP) through transcriptional editing. Proteolytic cleavage of the sGP precursor yields a mature sGP and a C-terminal Δ-peptide. $GP_{1,2}$ is displayed on the virus surface (in trimeric form, known as the "spike"), and is responsible for membrane attachment, virus internalisation and fusion. A domain schematic is provided in FIG. 1. The soluble glycoprotein sGP is secreted into the extracellular space. In a concept described as 'antigenic subversion' sGP has been proposed to induce a host antibody response that targets epitopes that sGP has in common with $GP_{1,2}$, thereby allowing sGP to bind and compete for anti-$GP_{1,2}$ antibodies. The editing has been observed in both in vitro and in vivo models of infection. A significant amount of $GP_{1,2}$ is shed from infected cells in a soluble form due to cleavage by cellular metalloprotease TACE at the amino acid position D637. It is also reported that the shed $GP_{1,2}$ and sGP binds to the TLR4 receptor, which leads to upregulation of cytokines. Over-stimulation of TLR 4 can lead to immune pathology and death, as in the case of septic shock which is a result of bacterial LPS binding to TLR 4. Without wishing to be bound by theory, inventors believe that shed $GP_{1,2}$ and sGP binds to TLR4 and causes release of cytokines that contribute to blood vessel leakage and inflammation.

The Filoviridae family includes the virus genera *Ebolavirus* and *Marburgvirus*. Due to its similar morphology and genetic arrangement, it is expected that *Cuevaviruses* will be classified as Filoviruses in the near future.

The genus *Marburgvirus* includes the *Marburg marburgvirus* species, whose members include *Marburg* virus (MARV) and Ravn virus (RAVV). The genus *Cuevavirus* is understood to include only the *Lloviu cuevavirus* species.

The *Ebolavirus* genus includes Ebola virus (EBOV, formerly designated Zaire ebolavirus), *Bundibugyo* virus (BDBV; otherwise known as *Bundibugyo ebolavirus* (BEBOV)), *Reston* virus (RESTV; otherwise known as *Reston ebolavirus* (REBOV)), *Sudan* virus (SUDV, otherwise known as *Sudan ebolavirus* (SEBOV)) and *Taï Forest ebolavirus* (TAFV, otherwise known as *Taï Forest ebolavirus* (TEBOV)). RESTV is the only known Filovirus that does not cause severe haemorrhagic disease in humans, however, it can be fatal in monkeys and has been recently recovered from infected swine in South-east Asia.

EBOV has the highest case fatality rate of the currently known *Ebolaviruses* (up to 90%). The most recent EBOV outbreak emerged in Southern Guinea in 2014, with fatality rates over 50%. This epidemic has now spread to Liberia, Sierra Leone and Nigeria, with one case reported in Senegal. Due to the high mortality rate, potential transmission from person-to-person contact and the lack of approved vaccines or anti-viral therapies, EBOV is classified as a hazard group 4 pathogen. The prototype Ebola virus is the Mayinga variant (EBOV/May).

There are at present no licensed therapeutics to treat EBOV disease (EBVD). Several pre-existing medicines have been considered for re-purposing as EBVD treatments, many of which are either undergoing testing or have already been tested in patients with EBVD. Several therapies have also been considered by the World Health Organisation (WHO), but these have been deemed inappropriate for further investigation. Drugs evaluated by the WHO Science and Technical Advisory Committee on Emergency Ebola Interventions (STAC-EE) are categorised as follows:

Drugs already under evaluation in formal clinical trials in West Africa. These include favipiravir (T705) and brincidofovir.

Drugs that have been prioritized for testing in human efficacy trials, but for which such trials are not yet underway. These trials may include the following: Zmapp, TKM-100802, AVI-7537, BCX-4430, and interferons.

Drugs that have already been given to patients for compassionate reasons or in ad hoc trials, including: Zmapp; amiodarone; favipiravir (T705); irbesartan+ atorvastatin +/−clomiphene; and FX06.

Drugs that demonstrate promising anti-Ebola activity in-vitro or in mouse models, but for which additional data should be generated prior to proceeding to clinical trials. These include: azithromycin; chloroquine; erlotinib/sunitinib; sertraline; and clomiphene.

Drugs that had been prioritised or considered for prioritisation and have now been deprioritized based on new data or more detailed analysis of old data. There is a single drug in this category, namely toremiphene.

Antibody-based products are showing promise in the current EBVD epidemic, and those currently undergoing investigation can be broadly divided into two categories:

(a) plasma derived from EBVD survivors: transfusion of convalescent whole blood and plasma has been prioritised for use as an investigational therapy in the current epidemic. Convalescent whole blood donated by patients who have recovered from EBVD is currently being administered in some Ebola treatment centres; and (b) neutralising monoclonal antibodies: whilst ZMapp has been used to treat humans with EBVD, although its efficacy is unknown.

Despite the significant and urgent need for additional EBVD therapeutics, the above-mentioned antibody-based products are hampered by significant limitations. For example, plasma obtained from patients who have recovered from EBVD contains a variety of immune components, and is therefore difficult to standardise. Also, because the active ingredient in these EBVD patient reparations is not defined, it is impossible to define the potency and reproducibility of such products. There also exists a risk of transferring other infections such as hepatitis or AIDS. Moreover, plasma obtained from patients is in very short supply.

Therapies based on monoclonal antibodies (mAbs) typically allow more accurate definition of the active agent and its potency, as compared to EBVD patient plasma, but mAb-based therapies are slow to develop and expensive, owing inter alia to the high manufacture costs. mAb-based therapeutics can be unsuitable for widespread application where healthcare funds are limited, and this is particularly the case in large-scale epidemics (such as the current EBVD epidemic). In addition to these financial constraints, the efficacy of mAb-based therapies can be greatly reduced if the prevalent virus undergoes a mutation in the antigenic region that is targeted by the mAb.

Accordingly, there is an urgent need for further therapeutics for the treatment and suppression of Filovirus disease, and particularly EBVD. There is also an urgent need for further therapeutics for prevention or suppression of Filovirus disease, and particularly EBVD.

The need for further therapeutics for the treatment, suppression and prevention of Filovirus disease, and particularly EBVD, is addressed by the present invention. The present invention also avoids many of the above-mentioned limitations associated with existing therapeutics.

The present invention is based on the surprising discovery that ovine antibodies raised against recombinant Filovirus glycoprotein are highly efficacious in vivo. In particular, the inventors have demonstrated that recombinant Filovirus glycoprotein expressed in a human cell line is highly immunogenic in the ovine host.

The present invention provides a composition comprising ovine, caprine, equine, or bovine antibodies wherein said antibodies bind to Filovirus glycoprotein. In one embodiment, the antibodies are ovine or caprine. In one embodiment, the antibodies are ovine, caprine or bovine.

In one embodiment, the Filovirus glycoprotein is selected from the list consisting of an *Ebolavirus* glycoprotein, a *Marburgvirus* glycoprotein, and a *Cuevavirus* glycoprotein. The glycoprotein is preferably an *Ebolavirus* glycoprotein, most preferably an Ebola virus glycoprotein.

In a preferred embodiment, the composition comprises ovine antibodies that bind to Ebola virus glycoprotein.

Although one or more monoclonal antibodies are optional, the antibody is preferably a polyclonal antibody.

An antibody that binds to a Filovirus glycoprotein is one capable of binding that glycoprotein with sufficient affinity such that the antibody is useful as a therapeutic agent. An antibody that binds to a glycoprotein of interest is one that binds to a Filovirus glycoprotein with an affinity ($K_a$) of at least $10^4$ M. Neutralising activity of a substance may be measured by its ability to reduce or prevent the death of mammalian cells grown in culture and exposed to Filovirus.

In one embodiment, the composition of the invention is for use in treating or suppressing a Filovirus disease/infection in a patient. In one embodiment, the invention provides use of the composition of the invention, in treating or suppressing a Filovirus disease in a patient. In one embodiment, the invention provides a method of treating or suppressing a Filovirus disease in a patient, said method comprising administering to a patient the antibody composition of the invention.

In one embodiment, the antibodies of the present invention are used prophylactically to prevent the onset of Filovirus disease. In such embodiments, the patient is typically at high risk of becoming infected with Filovirus, e.g. resident in an area of high Filovirus prevalence, exposed to or at risk of exposure to a second individual who has shown the clinical symptoms associated with Filovirus disease, or a corpse of such a subject, or a laboratory or medical worker. A "prophylactically effective amount" is any amount of the antibody that, when administered alone or in combination to a patient, inhibits or delays the onset or reoccurence of the Filovirus disease, or at least one of the clinical symptoms of Filovirus disease. In one embodiment, the prophylactically effective amount prevents the onset or reoccurence of the Filovirus disease entirely. "Inhibiting" the onset means either lessening the likelihood of the infection's onset, or preventing the onset entirely.

In one embodiment, the Filovirus disease is selected from the list consisting of *Ebolavirus* disease, *Marburgvirus* disease, and *Cuevavirus* disease. The Filovirus disease is preferably *Ebolavirus* disease, most preferably an Ebola virus disease (EBVD).

In a preferred embodiment, treating, suppressing or preventing Filovirus disease comprises intravenous administration of said composition to said patient. In another preferred embodiment, treating, suppressing or preventing Filovirus disease comprises intraperitoneal administration of said composition to said patient. In another preferred embodiment, treating, suppressing or preventing Filovirus disease comprises intramuscular administration of said composition to said patient. In another preferred embodiment, treating, suppressing or preventing Filovirus disease comprises oral administration of said composition to said patient.

The patient is typically a mammal, preferably a human.

A therapeutically effective amount refers to the amount of the antibody, which when administered alone or in combination to a patient for treating, suppressing or preventing Filovirus disease, or at least one of the clinical symptoms of Filovirus disease, is sufficient to affect such treatment of the infection, or symptom. The therapeutically effective amount can vary depending, for example, on the antibody, the infection, and/or symptoms of the infection, the severity of the infection, and/or the age, weight, and/or health of the patient to be treated, and the judgment of the prescribing physician. An appropriate therapeutically effective amount in any given instance may be ascertained by those skilled in the art or capable of determination by routine experimentation. A therapeutically effective amount is also one in which any toxic or detrimental effects of the antibody are outweighed by the beneficial effects. Routes of administration of immunoglobulin are known, for example in the treatment of rabies, and the treatment of patients infected with smallpox/monkeypox/vaccinia using hyperimmune serum raised in humans.

In one embodiment, treating or suppressing Filovirus disease comprises administering a composition of the invention to the patient within 5 days of infection with Filovirus. In one embodiment, the composition is administered to the patient within 2 days of infection, preferably within 1 day of infection with Filovirus, more preferably within 12 hours of infection with Filovirus, most preferably within 6 hours of infection with Filovirus. Said "infection with Filovirus" includes exposure to a second patient suffering from Filovirus disease or a sample suspected of containing, or known to contain Filovirus.

In one embodiment, treating or suppressing Filovirus disease comprises administering a composition of the invention to the patient within 5 days of displaying symptoms of Filovirus disease. In one embodiment, the composition is administered to the patient within 4 days of displaying symptoms of Filovirus disease. In one embodiment, the composition is administered within 3 days of displaying symptoms of Filovirus disease. In one embodiment, the composition is administered within 2 days of displaying symptoms of Filovirus disease, preferably within 1 day of displaying symptoms of Filovirus disease, more preferably within 12 hours of displaying symptoms of Filovirus disease, most preferably within 6 hours of displaying symptoms of Filovirus disease.

In one embodiment, treating or suppressing Filovirus disease comprises administering a composition of the invention to the patient 5 days or more after infection with Filovirus. In one embodiment, the composition is administered to the patient between 5-21 days after infection with Filovirus. In one embodiment, the composition is administered to the patient between 5-21 days after infection with Filovirus e.g. 5-21, 5-20, 5-19, 5-18, 5-17, 5-16, 5-15, 5-14, 5-13, 5-12, 5-11, 5-10, 5-9, 5-8, 5-7 or 5-6 days after infection with Filovirus. In one embodiment, the composition is administered to the patient between 6-21 days after infection with Filovirus e.g. 6-21, 6-20, 6-19, 6-18, 6-17, 6-16, 6-15, 6-14, 6-13, 6-12, 6-11, 6-10, 6-9, 6-8 or 6-7 days after infection with Filovirus. In one embodiment, the composition is administered to the patient between 7-21 days after infection with Filovirus e.g. 7-21, 7-20, 7-19, 7-18, 7-17, 7-16, 7-15, 7-14, 7-13, 7-12, 7-11, 7-10, 7-9, or 7-8 days after infection with Filovirus. In one embodiment, the composition is administered to the patient between 8-21 days after infection with Filovirus e.g. 8-21, 8-20, 8-19, 8-18, 8-17, 8-16, 8-15, 8-14, 8-13, 8-12, 8-11, 8-10 or 8-9 days after infection with Filovirus. In one embodiment, the composition is administered to the patient between 9-21 days after infection with Filovirus e.g. 9-21, 9-20, 9-19, 9-18, 9-17, 9-16, 9-15, 9-14, 9-13, 9-12, 9-11, or 9-10 days after infection with Filovirus. In one embodiment, the composition is administered to the patient between 10-21 days after infection with Filovirus e.g. 10-21, 10-20, 10-19, 10-18, 10-17, 10-16, 10-15, 10-14, 10-13, 10-12, or 10-11 days after infection with Filovirus. Typically the composition is administered to the patient within 5-9 days of infection. Said "infection with Filovirus" includes exposure to a second patient suffering from Filovirus disease or a sample suspected of containing, or known to contain Filovirus.

In one embodiment, treating or suppressing Filovirus disease comprises administering a composition of the invention to the patient 5 days or more after displaying symptoms of Filovirus disease. In one embodiment, the composition is administered to the patient between 5-10 days after displaying symptoms of Filovirus disease. In one embodiment, the composition is administered to the patient between 5-10 days after displaying symptoms of Filovirus disease e.g. 5-9, 5-8, 5-7, or 5-6 days after displaying symptoms of Filovirus disease. In one embodiment, the composition is administered to the patient between 6-10 days after displaying symptoms of Filovirus disease. In one embodiment, the composition is administered to the patient between 6-10 days after displaying symptoms of Filovirus disease e.g. 6-9, 6-8 or 6-7 days after displaying symptoms of Filovirus disease. In one embodiment, the composition is administered to the patient between 7-10 days after displaying symptoms of Filovirus disease. In one embodiment, the composition is administered to the patient between 7-10 days after displaying symptoms of Filovirus disease e.g. 7-9 or 7-8 days after displaying symptoms of Filovirus disease.

In one embodiment, preventing Filovirus disease comprises administering a composition of the invention to the patient prior to infection with Filovirus, and before presentation of symptoms of Filovirus disease. In one embodiment, the composition is administered to the patient within 1 day of infection with Filovirus. In one embodiment, the composition is administered to the patient within 2 days of infection with Filovirus. In one embodiment, the composition is administered to the patient within 3 days of infection with Filovirus. In one embodiment, the composition is administered to the patient within 4 days of infection with Filovirus. In one embodiment, the composition is administered to the patient within 5 days of infection with Filovirus. In one embodiment, the composition is administered to the patient within 6 days of infection with Filovirus. In one embodiment, the composition is administered to the patient within 7 days of infection with Filovirus.

The efficacious antibodies of the invention simultaneously bind to the $GP_{1,2}$ cell surface "spike" protein and also to the soluble sGP protein. Binding to the cell surface spike protein leads to clearance of Filovirus from the patient. Binding to the sGP neutralises the immunopathogenic effects of Filovirus infection. Without wishing to be bound by theory, the inventors believe that the immunopathogenic effects of Filovirus infection are neutralised by blocking the activation of TLR4.

The glycoprotein can be from any member of the Filovirus family, and the advantageous technical effects observed herein would be obtained following immunisation with any of the recombinant glycoproteins identified in Table 1:

TABLE 1

Non-limiting list of Filovirus glycoproteins

| Filovirus | Reference sequence |
| --- | --- |
| EBOV | Genbank: AAB81004.1 |
| BDBV | NCBI: YP_003815435.1 |
| RESTV | Genbank: BAB69006.1 |
| SUDV | UniProtKB/Swiss-Prot: Q66814.1 |
| TAFV | UniProtKB/Swiss-Prot: Q66810.1 |
| MARV | GenBank: AJD39285.1 |
| RAVV | UniProtKB/Swiss-Prot: Q1PDC7.1 |

Further Filovirus glycoprotein sequences are readily identifiable.

An exemplary Filovirus glycoprotein is the polypeptide of SEQ ID NO: 1.

In one embodiment the Ebola virus glycoprotein comprises an amino acid sequence having 70% or more identity to SEQ ID NO: 1, and comprises an epitope of SEQ ID NO: 1. Thus, in one embodiment, the Ebola virus glycoprotein comprises or consists of an amino acid sequence: (a) having 70% or more identity (e.g. 70%, 75%, 80%, 85%, 90%, 91%, 92%, 93%, 94%, 95%, 96%, 97%, 98%, 98.5%, 99%, 99.5%, 99.8%, 99.9%, or more) to SEQ ID NO: 1, while retaining at least one epitope of SEQ ID NO: 1. Preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 21, 22, 23, 24, 25 or 26 or more) from the N-terminus of SEQ ID NO: 1 while retaining at least one epitope of SEQ ID NO: 1. Amino acid fragments of Ebola virus glycoprotein may thus comprise an amino acid sequence of e.g. up to 30, up to 40, up to 50, up to 60, up to 70, up to 80, up to 90, up to 100, up to 125, up to 150, up to 175, up to 200, up to 250, up to 300, up to 350, up to 400, up to 450, up to 500, up to 550, up to 600, or up to 650 consecutive amino acid residues of SEQ ID NO: 1, while retaining at least one epitope of SEQ ID NO: 1.

In one embodiment the Ebola virus glycoprotein comprises an amino acid sequence having 70% or more identity to an amino acid sequence referred to in Table 1, and comprises an epitope of the corresponding endogenous amino acid sequence. Thus, in one embodiment, the Ebola virus glycoprotein comprises or consists of an amino acid sequence: (a) having 70% or more identity (e.g. 70%, 75%, 80%, 85%, 90%, 91%, 92%, 93%, 94%, 95%, 96%, 97%, 98%, 98.5%, 99%, 99.5%, 99.8%, 99.9%, or more) to an amino acid sequence referred to in Table 1, while retaining at least one epitope of the corresponding endogenous amino acid sequence. Preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 21, 22, 23, 24, 25 or 26 or more) from the N-terminus of an amino acid sequence referred to in Table 1 while retaining at least one epitope of the corresponding endogenous amino acid sequence. Amino acid fragments of Ebola virus glycoprotein may thus comprise an amino acid sequence of e.g. up to 30, up to 40, up to 50, up to 60, up to 70, up to 80, up to 90, up to 100, up to 125, up to 150, up to 175, up to 200, up to 250, up to 300, up to 350, up to 400, up to 450, up to 500, up to 550, up to 600, or up to 650 consecutive amino acid residues of an amino acid sequence referred to in Table 1, while retaining at least one epitope of the corresponding endogenous amino acid sequence.

The invention also provides an immunogenic composition comprising recombinant Filovirus glycoprotein, wherein said Filovirus glycoprotein lacks the endogenous transmembrane domain (corresponding to amino acid residues 651-671 in SEQ ID NO: 1). The invention also provides an immunogenic composition comprising recombinant Filovirus glycoprotein, wherein said Filovirus glycoprotein lacks the endogenous transmembrane domain and lacks the membrane-proximal external region. The skilled person can easily identify the transmembrane domains of other Filovirus glycoproteins. Similarly, the skilled person can easily identify the membrane-proximal external region of other Filovirus glycoproteins. An exemplary Filovirus glycoprotein which lacks the endogenous transmembrane domain is the polypeptide of SEQ ID NO: 2, which corresponds to the polypeptide of SEQ ID NO: 1, but without the endogenous transmembrane domain. The polypeptide of SEQ ID NO: 2 also lacks the endogenous membrane-proximal external region that is present in SEQ ID NO: 1 (corresponding to amino acid residues 633-650 of SEQ ID NO: 1), and is thus also an exemplary Filovirus glycoprotein which lacks the endogenous transmembrane domain and lacks the endogenous membrane-proximal external region. The polypeptide of SEQ ID NO: 2 also lacks a very short cytoplasmic tail (corresponding to amino acid residues 672-676 of SEQ ID NO: 1). Thus, in one embodiment, preferred Filovirus glycoproteins lack the endogenous transmembrane domain. In one embodiment, preferred Filovirus glycoproteins lack the endogenous transmembrane domain and lack the endogenous membrane-proximal external region. As is well known to the skilled person, expression of Filovirus glycoprotein in a eukaryotic cell typically leads to cleavage of the signal peptide by signal peptidases. Thus, in some embodiments, the Filovirus glycoprotein also lacks the signal peptide. Thus, in one embodiment, preferred Filovirus glycoproteins lack the endogenous transmembrane domain and the signal peptide. In one embodiment, preferred Filovirus glycoproteins lack the endogenous transmembrane domain, the endogenous membrane-proximal external region, and the signal peptide.

In one embodiment the Ebola virus glycoprotein comprises an amino acid sequence having 70% or more identity to SEQ ID NO: 2, and comprises an epitope of SEQ ID NO: 2. Thus, in one embodiment, the Ebola virus glycoprotein comprises or consists of an amino acid sequence: (a) having 70% or more identity (e.g. 70%, 75%, 80%, 85%, 90%, 91%, 92%, 93%, 94%, 95%, 96%, 97%, 98%, 98.5%, 99%, 99.5%, 99.8%, 99.9%, or more) to SEQ ID NO: 2, while retaining at least one epitope of SEQ ID NO: 2. Preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 21, 22, 23, 24, 25 or 26 or more) from the N-terminus of SEQ ID NO: 2 while retaining at least one epitope of SEQ ID NO: 2. Amino acid fragments of Ebola virus glycoprotein lacking the endogenous transmembrane domain may thus comprise an amino acid sequence of e.g. up to 30, up to 40, up to 50, up to 60, up to 70, up to 80, up to 90, up to 100, up to 125, up to 150, up to 175, up to 200, up to 250, up to 300, up to 350, up to 400, up to 450, up to 500, up to 550, up to 600, or up to 650 consecutive amino acid residues of SEQ ID NO: 2, while retaining at least one epitope of SEQ ID NO: 2.

In one embodiment the Ebola virus glycoprotein comprises an amino acid sequence having 70% or more identity to an amino acid sequence referred to in Table 1, and comprises an epitope of the corresponding endogenous amino acid sequence, but lacking the endogenous transmembrane domain. Thus, in one embodiment, the Ebola virus glycoprotein comprises or consists of an amino acid sequence: (a) having 70% or more identity (e.g. 70%, 75%, 80%, 85%, 90%, 91%, 92%, 93%, 94%, 95%, 96%, 97%, 98%, 98.5%, 99%, 99.5%, 99.8%, 99.9%, or more) to an amino acid sequence referred to in Table 1, while retaining at least one epitope of the corresponding endogenous amino acid sequence, but lacking the endogenous transmembrane domain. Preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 21, 22, 23, 24, 25 or 26 or more) from the N-terminus of an amino acid sequence referred to in Table 1 while retaining at least one epitope of the corresponding endogenous amino acid sequence, but lacking the endogenous transmembrane domain. Amino acid fragments of Ebola virus glycoprotein may thus comprise an amino acid sequence of e.g. up to 30, up to 40, up to 50, up to 60, up to 70, up to 80, up to 90, up to 100, up to 125, up to 150, up to 175, up to 200, up to 250, up to 300, up to 350, up to 400, up to 450, up to 500, up to 550, up to 600, or up to 650 consecutive amino acid residues of an amino acid sequence referred to in Table 1, while retaining at least one epitope of the corresponding endogenous amino acid sequence, but lacking the endogenous transmembrane domain.

In one embodiment the Ebola virus glycoprotein comprises an amino acid sequence having 70% or more identity to an amino acid sequence referred to in Table 1, and comprises an epitope of the corresponding endogenous amino acid sequence, but lacking the endogenous transmembrane domain and the endogenous membrane-proximal external region. Thus, in one embodiment, the Ebola virus glycoprotein comprises or consists of an amino acid sequence: (a) having 70% or more identity (e.g. 70%, 75%, 80%, 85%, 90%, 91%, 92%, 93%, 94%, 95%, 96%, 97%, 98%, 98.5%, 99%, 99.5%, 99.8%, 99.9%, or more) to an amino acid sequence referred to in Table 1, while retaining at least one epitope of the corresponding endogenous amino acid sequence, but lacking the endogenous transmembrane domain and the endogenous membrane-proximal external region. Preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 21, 22, 23, 24, 25 or 26 or more) from the N-terminus of an amino acid sequence referred to in Table 1 while retaining at least one epitope of the corresponding endogenous amino acid sequence, but lacking the endogenous transmembrane domain and the endogenous membrane-proximal external region. Amino acid fragments of Ebola virus glycoprotein may thus comprise an amino acid sequence of e.g. up to 30, up to 40, up to 50, up to 60, up to 70, up to 80, up to 90, up to 100, up to 125, up to 150, up to 175, up to 200, up to 250, up to 300, up to 350, up to 400, up to 450, up to 500, up to 550, up to 600, or up to 650 consecutive amino acid residues of an amino acid sequence referred to in Table 1, while retaining at least one epitope of the corresponding endogenous amino acid sequence, but lacking the endogenous transmembrane domain and the endogenous membrane-proximal external region.

The invention also provides an immunogenic composition comprising recombinant Filovirus glycoprotein for use in raising an immune response in a mammal, wherein said Filovirus glycoprotein lacks the endogenous transmembrane domain. The invention also provides use of a filovirus glycoprotein in raising an immune response in a mammal, wherein said Filovirus glycoprotein lacks the endogenous transmembrane domain. The invention also provides an immunogenic composition comprising recombinant Filovirus glycoprotein for use in raising an immune response in a mammal, wherein said Filovirus glycoprotein lacks the endogenous transmembrane domain and the endogenous membrane-proximal external region. The invention also provides use of a filovirus glycoprotein in raising an immune response in a mammal, wherein said Filovirus glycoprotein lacks the endogenous transmembrane domain and the endogenous membrane-proximal external region. The Filovirus is typically an *Ebolavirus*, preferably Ebola virus. The mammal is preferably selected from the list consisting of ovine, caprine, equine and bovine.

The invention also provides nucleic acid encoding a Filovirus glycoprotein as defined herein. In one embodiment, the nucleic acid comprises SEQ ID NO: 3. In one embodiment, the nucleic acid sequence has 70% or more identity to SEQ ID NO: 3 (e.g. 70%, 75%, 80%, 85%, 90%, 91%, 92%, 93%, 94%, 95%, 96%, 97%, 98%, 98.5%, 99%, 99.5%, 99.8%, 99.9%, or more) to SEQ ID NO: 3. Preferred fragments lack one or more nucleic acids (e.g. 1, 2, 3, 4, 5, 6, 7, 8, 9, 10, 15, 20, 25 or more) from the 5' end and/or one or more nucleic acids (e.g. 1, 2, 3, 4, 5, 6, 7, 8, 9, 10, 15, 20, 21, 22, 23, 24, 25 or 26 or more) from the 3' end of SEQ ID NO: 3.

The invention also provides nucleic acid encoding a Filovirus glycoprotein as defined herein. In one embodiment, the nucleic acid comprises SEQ ID NO: 4. In one embodiment, the nucleic acid sequence has 70% or more identity to SEQ ID NO: 4, (e.g. 70%, 75%, 80%, 85%, 90%, 91%, 92%, 93%, 94%, 95%, 96%, 97%, 98%, 98.5%, 99%, 99.5%, 99.8%, 99.9%, or more) to SEQ ID NO: 4. Preferred fragments lack one or more nucleic acids (e.g. 1, 2, 3, 4, 5, 6, 7, 8, 9, 10, 15, 20, 25 or more) from the 5' end and/or one or more nucleic acids (e.g. 1, 2, 3, 4, 5, 6, 7, 8, 9, 10, 15, 20, 21, 22, 23, 24, 25 or 26 or more) from the 3' end of SEQ ID NO: 4.

In one embodiment, the nucleic acid has been optimised for expression. In one embodiment, the nucleic acid comprises SEQ ID NO: 5. In one embodiment, the nucleic sequence has 70% or more identity to SEQ ID NO: 5 (e.g. 70%, 75%, 80%, 85%, 90%, 91%, 92%, 93%, 94%, 95%, 96%, 97%, 98%, 98.5%, 99%, 99.5%, 99.8%, 99.9%, or more) to SEQ ID NO: 5. Preferred fragments lack one or more nucleic acids (e.g. 1, 2, 3, 4, 5, 6, 7, 8, 9, 10, 15, 20, 25 or more) from the 5' end and/or one or more nucleic acids (e.g. 1, 2, 3, 4, 5, 6, 7, 8, 9, 10, 15, 20, 21, 22, 23, 24, 25 or 26 or more) from the 3' end of SEQ ID NO: 5.

The invention also provides a vector comprising a promoter operatively liked to nucleic acid as defined above. In one embodiment, the vector is a pDISPLAY vector. Other suitable vectors are readily identifiable. For example, in one embodiment, the vector is a pHLsec expression vector.

The invention also provides a human cell capable of protein expression comprising a vector as described above. In one embodiment, the human cell is a HEK293T cell. The invention also provides a recombinant Filovirus glycoprotein obtainable from a human cell. Expression of Filovirus glycoprotein in a mammalian cell advantageously yields significant levels of glycoprotein, which is highly desirable for use in immunisation. The inventors also found that Filovirus glycoprotein expressed in human cells are advantageously immunogenic in an ovine host. Filovirus glycoprotein expressed in human cells, preferably HEK293T cells, more closely represents the in vivo glycosylation pattern of the Filovirus glycoprotein during infection (than does e.g. expression in a prokaryotic host). Accordingly, Filovirus glycoproteins of the invention preferably comprise the endogenous mucin domain (corresponding to amino acids 313-464 of SEQ ID NO:1). Similarly, Filovirus glycoproteins of the invention preferably comprise the endogenous O- and N-linked glycosylation sites. Although the signal peptide is not typically present in the mature glycoprotein when expressed in a eukaryotic cell (due to cleavage by signal peptidases and cellular degradation), expression of the endogenous signal peptide is preferred, because it is believed to modulate the incorporation of high-mannose carbohydrates into e.g. EBOV glycoprotein.

The invention also provides a method of producing antibodies in a host selected from the list comprising ovine, caprine, equine, and bovine said method comprising (i) administering to a sheep, goat, horse or cow the Filovirus glycoprotein as defined above, (ii) allowing sufficient time for the generation of antibodies in the sheep, goat, horse or cow, and (iii) obtaining the antibodies from the sheep, goat, horse or cow.

The method of the invention advantageously produces very high neutralising titres. Thus, the antibodies of the present invention can be readily obtained and can protect the patient against the pathological effects of Filovirus disease.

In use, the antibodies of the invention bind to a Filovirus GP1,2 on the surface of the Filovirus, preferably allowing clearance of the Filovirus from the patient. In use, the antibodies of the invention also bind to the immunopathogenic soluble form of the Filovirus glycoprotein (sGP), preferably neutralising its biological activity. Accordingly, the antibodies of the present invention are capable of treating or suppressing Filovirus disease. The antibodies of the present invention are also capable of preventing Filovirus disease.

The antibodies of the present invention interact with specific epitopes of Filovirus glycoprotein. With reference to Ebola virus glycoprotein (see SEQ ID NO: 1), an antibody can bind an epitope in the signal peptide (e.g. between amino acids 1-32), or in the GP1 base (e.g. corresponding to amino acids 33-70, 95-105, 158-168, 176-190), or in the GP1 head (e.g. corresponding to amino acids 71-95, 105-158, 168-176, 178-176, 214-227), or in the GP1 glycan cap (e.g. corresponding to amino acids 227-313), or in the mucin domain (e.g. corresponding to amino acids 313-464), or in the internal fusion loop (e.g. corresponding to amino acids 511-554), or in the heptad repeat 1 (e.g. corresponding to amino acids 554-599), or in the heptad repeat 2 (e.g. corresponding to amino acids 599-632), or in the membrane-proximal external region (corresponding to amino acids 633-650). With reference to Ebola virus glycoprotein lacking the endogenous transmembrane domain and the endogenous membrane-proximal external region (see SEQ ID NO: 2), an antibody can bind an epitope in the signal peptide (e.g. between amino acids 1-32), or in the GP1 base (e.g. corresponding to amino acids 33-70, 95-105, 158-168, 176-190), or in the GP1 head (e.g. corresponding to amino acids 71-95, 105-158, 168-176, 178-176, 214-227), or in the GP1 glycan cap (e.g. corresponding to amino acids 227-313), or in the mucin domain (e.g. corresponding to amino acids 313-464), or in the internal fusion loop (e.g. corresponding to amino acids 511-554), or in the heptad repeat 1 (e.g. corresponding to amino acids 554-599), or in the heptad repeat 2 (e.g. corresponding to amino acids 599-632).

In one embodiment, polyclonal antibodies of the invention can bind an epitope in the signal peptide (e.g. between amino acids 1-32 of SEQ ID NO: 1 or SEQ ID NO: 2); in the GP1 base (e.g. corresponding to amino acids 33-70, 95-105, 158-168, 176-190 of SEQ ID NO: 1 or SEQ ID NO: 2); in the GP1 head (e.g. corresponding to amino acids 71-95, 105-158, 168-176, 178-176, 214-227 of SEQ ID NO: 1 or SEQ ID NO: 2); in the GP1 glycan cap (e.g. corresponding to amino acids 227-313 of SEQ ID NO: 1 or SEQ ID NO: 2); in the mucin domain (e.g. corresponding to amino acids 313-464 of SEQ ID NO: 1 or SEQ ID NO: 2); in the internal fusion loop (e.g. corresponding to amino acids 511-554 of SEQ ID NO: 1 or SEQ ID NO: 2); in the heptad repeat 1 (e.g. corresponding to amino acids 554-599 of SEQ ID NO: 1 or SEQ ID NO: 2); and in the heptad repeat 2 (e.g. corresponding to amino acids 599-632 of SEQ ID NO: 1 or SEQ ID NO: 2). In a preferred embodiment, such polyclonal antibodies do not bind to epitopes present in the membrane-proximal external region (corresponding to amino acids 633-650 of SEQ ID NO: 1), or in the transmembrane domain (corresponding to amino acids 651-671 of SEQ ID NO: 1).

As noted above, in some embodiments the Filovirus glycoprotein lacks the signal peptide (e.g. where the Filovirus glycoprotein was expressed in a eukaryotic cell). The skilled person will immediately recognise that antibodies of the invention raised against such Filovirus glycoproteins are not expected to bind to an epitope in the signal peptide (e.g. between amino acids 1-32 of SEQ ID NO: 1 or SEQ ID NO: 2). Thus, in one embodiment, polyclonal antibodies of the invention can bind an epitope in the GP1 base (e.g. corresponding to amino acids 33-70, 95-105, 158-168, 176-190 of SEQ ID NO: 1 or SEQ ID NO: 2); in the GP1 head (e.g. corresponding to amino acids 71-95, 105-158, 168-176, 178-176, 214-227 of SEQ ID NO: 1 or SEQ ID NO: 2); in the GP1 glycan cap (e.g. corresponding to amino acids 227-313 of SEQ ID NO: 1 or SEQ ID NO: 2); in the mucin domain (e.g. corresponding to amino acids 313-464 of SEQ ID NO: 1 or SEQ ID NO: 2); in the internal fusion loop (e.g. corresponding to amino acids 511-554 of SEQ ID NO: 1 or SEQ ID NO: 2); in the heptad repeat 1 (e.g. corresponding to amino acids 554-599 of SEQ ID NO: 1 or SEQ ID NO: 2); and in the heptad repeat 2 (e.g. corresponding to amino acids 599-632 of SEQ ID NO: 1 or SEQ ID NO: 2). In a preferred embodiment, such polyclonal antibodies do not bind to epitopes present in the membrane-proximal external region (corresponding to amino acids 633-650 of SEQ ID NO: 1), or in the transmembrane domain (corresponding to amino acids 651-671 of SEQ ID NO: 1).

Where the invention concerns an "epitope", this epitope may be a B-cell epitope and/or a T-cell epitope. Such epitopes can be identified empirically (e.g. using PEPSCAN or similar methods), or they can be predicted {e.g. using the Jameson-Wolf antigenic index, matrix-based approaches, MAPITOPE, TEPITOPE, neural networks, OptiMer & EpiMer, ADEPT, Tsites, hydrophilicity, antigenic index or other methods known in the art). Epitopes are the parts of an immunogen that are recognised by and bind to the antigen binding sites of antibodies or T-cell receptors, and they may also be referred to as "antigenic determinants".

Antibodies of the present invention may bind to and/or neutralise a Filovirus glycoprotein from member(s) of a different family. Due to higher sequence homology within Filoviridae families, antibodies of the present invention may bind to and/or neutralise a Filovirus glycoprotein from the same Filovirus family.

In certain embodiments, the antibodies of the present invention bind to and/or neutralise Filovirus glycoprotein with an amino acid sequence at least 80%, 85%, 90%, 95%, 98%, 99%, or more identical to SEQ ID NO: 1.

In certain embodiments, the antibodies of the present invention bind to and/or neutralise Filovirus glycoprotein with an amino acid sequence at least 80%, 85%, 90%, 95%, 98%, 99%, or more identical to SEQ ID NO: 2.

In certain embodiments, the antibodies of the present invention bind to and/or neutralise Filovirus glycoprotein with an amino acid sequence at least 80%, 85%, 90%, 95%, 98%, 99%, or more identical to a Filovirus glycoprotein sequence referred to in Table 1.

The invention also embraces a corresponding method for treatment, suppression or prevention of Filoviridae infection. Said method of treatment, suppression or prevention comprises administration of the antibody composition of the present invention to a patient.

The patient can be infected with a Filovirus, or have a symptom of Filovirus disease (e.g. severe haemorrhagic fever, and including sudden onset of fever, chills, headache, myalgia, and anorexia, which may be followed by abdominal pain, sore throat, nausea, vomiting, cough, arthralgia, diarrhoea, and pharyngeal and conjunctival vasodilatation) or have a predisposition towards Filovirus disease (e.g. residence in an area of high Filovirus prevalence, exposure to a second individual who has shown the clinical symptoms associated with Filovirus disease or medical worker). The present invention thereby provides an effective means for preventing, suppressing or treating Filovirus disease (or a symptom thereof).

In one embodiment, the method of treating Filovirus disease comprises administering antibody of the invention systemically (eg. once or twice per day, or once or twice or 3- or 4-times per every 3-4 days; for a short period of typically 1-2 weeks) followed by a more prolonged period of administration (eg. once or twice or 3- or 4- or 5- or 6-times per day, or once or twice or 3- or 4- or 5- or 6-times per every 3-4 days, or once or twice or 3- or 4- or 5- or 6-times per week) of antibody. Administration routes include subcutaneous, intramuscular, intraperitoneal, and intravenous. Administration routes include subcutaneous, intramuscular, intraperitoneal, intravenous and oral. The administration route is preferably intravenous, intramuscular or intraperitoneal. The administration route is preferably intravenous, intramuscular, intraperitoneal or oral.

Naturally, when administered systemically, the antibodies are formulated accordingly (eg. such formulations are typically provided as isotonic aqueous formulations and do not require means for protection against stomach acid or stomach enzymes such as trypsin and/or chymotrypsin).

Antibody Preparation

Ovine Antibodies

The ovine antibodies are antibodies which have been raised in a sheep. Thus, the present invention includes a method of producing ovine antibodies for use in the antibody composition of the invention, said method generally involving (i) administering an immunogen comprising Filovirus glycoprotein, or a fragment thereof to a sheep, (ii) allowing sufficient time for the generation of antibodies in the sheep, and (iii) obtaining the antibodies from the sheep. As used herein, sheep comprise any species that fall within the *Ovis* genus (e.g. *Ovis ammon, Ovis orientalis aries, Ovis orientalis orientalis, Ovis orientalis vignei, Ovis Canadensis, Ovis dalli, Ovis nivicola*).

The antibody may be obtained from the sheep serum. Thus, the procedures generate sheep antisera containing antibodies capable of binding and neutralising Filovirus glycoprotein. In a further embodiment, the antibodies are isolated and/or purified. Thus, another aspect of the present invention involves purifying the antibodies from sheep antiserum.

An ovine antibody is an antibody that has at least 100%, 99%, 95%, 90%, 80%, 75%, 60%, 50%, 25% or 10% amino acid sequence identity to an antibody that has been raised in a sheep.

Caprine Antibodies

The caprine antibodies are antibodies which have been raised in a goat. Thus, the present invention includes a method of producing caprine antibodies for use in the antibody composition of the invention, said method generally involving (i) administering an immunogen comprising Filovirus glycoprotein, or a fragment thereof to a goat, (ii) allowing sufficient time for the generation of antibodies in the goat, and (iii) obtaining the antibodies from the goat. As used herein, the term "goat" comprises any species that fall within the *Capra* genus (e.g. *Capra caucasica, Capra caucasica cylindricornis, Capra falconeri, Capra aegagrus, Capra aegagrus hircus, Capra ibex, Capra nubiana, Capra pyrenaica, Capra sibirica, Capra walie*).

The antibody may be obtained from the goat serum. Thus, the procedures generate goat antisera containing antibodies capable of binding and neutralising Filovirus glycoprotein. In a further embodiment, the antibodies are isolated and/or purified. Thus, another aspect of the present invention involves purifying the antibodies from goat antiserum.

A caprine antibody is an antibody that has at least 100%, 99%, 95%, 90%, 80%, 75%, 60%, 50%, 25% or 10% amino acid sequence identity to an antibody that has been raised in a goat.

Equine Antibodies

The equine antibodies are antibodies which have been raised in a horse. Thus, the present invention includes a method of producing equine antibodies for use in the antibody composition of the invention, said method generally involving (i) administering an immunogen comprising Filovirus glycoprotein, or a fragment thereof to a horse, (ii) allowing sufficient time for the generation of antibodies in the horse, and (iii) obtaining the antibodies from the horse. As used herein, the term "horse" comprises any species that fall within the *Equus* genus (e.g. *Equus ferus, Equus ferus caballus, Equus ferus ferus, Equus ferus przewalskii, Equus algericus, Equus lambei, Equus niobrarensis, Equus andium, Equus neogeus, Equus fraternus, Equus santaeelenae, Equus scotti, Equus niobrarensis, Equus conversidens, Equus francisci, Equus semiplicatus*).

The antibody may be obtained from the horse serum. Thus, the procedures generate horse antisera containing antibodies capable of binding and neutralising Filovirus glycoprotein. In a further embodiment, the antibodies are isolated and/or purified. Thus, another aspect of the present invention involves purifying the antibodies from horse antiserum.

A horse antibody is an antibody that has at least 100%, 99%, 95%, 90%, 80%, 75%, 60%, 50%, 25% or 10% amino acid sequence identity to an antibody that has been raised in a horse.

Bovine Antibodies

The bovine antibodies are antibodies which have been raised in a cow. Thus, the present invention includes a method of producing bovine antibodies for use in the antibody composition of the invention, said method generally involving (i) administering an immunogen comprising Filovirus glycoprotein, or a fragment thereof to a cow, (ii) allowing sufficient time for the generation of antibodies in the cow, and (iii) obtaining the antibodies from the cow. As used herein, the term "cow" comprises any species that fall within the *Bos* genus (e.g. *Bos taurus, Bos primigenius, Bos indicus, Bos aegyptiacus, Bos acutifrons, Bos planifrons, Bos gaurus, Bos frontalis, Bos javanicus, Bos palaesondaicus, Bos sauveli, Bos grunniens*).

The antibody may be obtained from the cow serum. Thus, the procedures generate cow antisera containing antibodies capable of binding and neutralising Filovirus glycoprotein. In a further embodiment, the antibodies are isolated and/or purified. Thus, another aspect of the present invention involves purifying the antibodies from cow antiserum.

A cow antibody is an antibody that has at least 100%, 99%, 95%, 90%, 80%, 75%, 60%, 50%, 25% or 10% amino acid sequence identity to an antibody that has been raised in a cow.

In one embodiment, the cow is engineered with a human immunoglobulin repertoire. Such cows may be used to generate antibodies (e.g. polyclonal antibodies) having a human backbone. Advantageously, such antibodies have a more optimal pk, and would not induce anti-immunoglobulin response.

Immunogens may be formulated with an adjuvant. Suitable adjuvants may include alum (aluminium phosphate or aluminium hydroxide), which is used widely in humans, and other adjuvants such as saponin and its purified component Quil A, Freund's complete and incomplete adjuvant, RIBBI adjuvant, and other adjuvants used in research and veterinary applications.

The method of producing antibodies allows all modes of immunisation (ie. to generate the antibodies of the invention), including subcutaneous, intramuscular, intraperitoneal, and intravenous. The invention also contemplates a wide variety of immunisation schedules. In one embodiment, a sheep or goat or horse or cow is administered immunogen on day zero and subsequently receives immunogen at intervals thereafter. It will be appreciated that the interval range and dosage range required depends on the route of administration, the nature of the formulation, and the judgement of the attending person. Variations in these dosage levels can be adjusted using standard empirical routines for optimisation. Similarly, it is not intended that the present invention be limited to any particular schedule for collecting antibody. The preferred collection time is someday after day 56. Levels of the specific antibody, i.e. that which binds to the immunogen, preferably represents at least 3 g per litre of serum.

The antibodies of the invention may be modified as necessary after collection, so that, in certain instances, they are less immunogenic in the patient to whom they are administered, and/or have a larger volume of distribution. For example, if the patient is a human, the antibodies may be despeciated by methods well known in the art. One example as to how an antibody can be made less immunogenic is to prepare the F(ab)$_2$ or Fab fragment. The antibodies of the invention may be used to produce such antibody fragments for which various techniques have been developed. For example, the fragments may be derived by proteolytic digestion of intact antibodies. Other techniques for their production will be apparent to the skilled practitioner.

Antibody Formulation and Delivery

In use, the present invention employs a composition, comprising the antibody composition of the present invention in a form suitable administration. The purified intact antibodies, or their fragments, are formulated for such delivery. For example, antibody, or its fragment, at a concentration between 5-50 or 15-50 or 25-50 or 500-100 g/litre may be formulated in buffer. Examples of suitable buffer components include physiological salts such as sodium citrate and/or citric acid. Preferred buffers contain 100-200 or 125-175 or approximately 150 (eg. 153) mM physiological salts such as sodium chloride.

In preparing compositions of the invention, the antibodies and/or fragments thereof can be dissolved in a vehicle, and sterilised, for example by filtration through a sterile filter using aseptic techniques, before filling into suitable sterile vials or ampoules and sealing. Advantageously additives such as buffering, solubilising, stabilising, preservative or bactericidal or suspending and/or local anaesthetic agents may be dissolved in the vehicle.

Dry powders, which are dissolved or suspended in a suitable vehicle prior to use, may be prepared by filling pre-sterilised ingredients into a sterile container using aseptic technique in a sterile area. Alternatively the ingredients may be dissolved into suitable containers using aseptic technique in a sterile area. The product is then freeze dried and the containers are sealed aseptically.

The dosage ranges for administration of the antibodies of the present invention are those to produce the desired therapeutic effect. It will be appreciated that the dosage range required depends on the precise nature of the antibody or composition, the nature of the formulation, the age of the patient, the nature, extent or severity of the patient's condition, contraindications, if any, and the judgement of the attending physician. Variations in these dosage levels can be adjusted using standard empirical routines for optimisation.

In one embodiment, typical daily dosages are in the range of 5-20 mg (e.g. 8-15 mg or approximately 10 mg) per kg of body weight. The unit dosage can vary from less than 100 mg to 3.5 g per dose, but typically will be in the region of 500 to 1000 mg, which may be administered daily, or more frequently (eg. 1×, 2×, 3× or 4× per day) or less frequently (e.g. on alternative days, or say once per week).

Combination Treatment

In one embodiment, antibodies of the invention are prepared and/or used in combination with one or more additional Filovirus disease therapeutic(s). Preferably, the additional Filovirus disease therapeutic(s) target a different component or mechanism of Filovirus (i.e. target a component or mechanism that is not related to the Filovirus glycoprotein). Compositions of the invention may thus also comprise one or more additional Filovirus disease therapeutic(s).

In one embodiment, the invention provides treatment, suppression or prevention, comprising administration of a combination of antibodies and additional therapeutic as defined above. Said treatment, suppression or prevention may be carried out in any way as deemed necessary or convenient by the person skilled in the art and for the purpose of this specification, no limitations with regard to the order, amount, repetition or relative amount of the compounds to be used in combination is contemplated.

Thus, in one embodiment, the invention provides treatment, suppression or prevention, comprising administration of a combination of antibodies and one or more additional therapeutics selected from the group consisting of: favipiravir (T705), brincidofovir, Zmapp, TKM-100802, AVI-7537, BCX-4430, interferons, irbesartan+atorvastatin+/−clomiphene, FX06, azithromycin, chloroquine, erlotinib/sunitinib, sertraline, and clomiphene. Said one or more additional therapeutic. In a preferred embodiment, antibodies of the invention are used in combination with another therapeutic that targets a different component of EBOV. For example, in one embodiment, ovine antibodies of the invention are used in combination with another therapeutic that targets a different component of EBOV. A preferred additional therapeutic is Favipiravir, which is an RNA polymerase inhibitor. Thus, in a preferred embodiment, the invention provides treatment, suppression or prevention, comprising administration of an ovine antibody and Favipiravir.

Definitions Section

Unless otherwise stated, the term "Filovirus glycoprotein" embraces the full length Filovirus glycoprotein, as well as Filovirus glycoprotein lacking the endogenous transmembrane domain. The term "Filovirus glycoprotein" also embraces fragments and variants of the same. Thus, the term "Filovirus glycoprotein" also embraces Filovirus glycoprotein lacking the endogenous transmembrane domain and the membrane-proximal external region. The term "Filovirus glycoprotein" also embraces filovirus glycoprotein lacking the signal peptide.

The term "lacking the endogenous transmembrane domain" means that the endogenous transmembrane domain is not present in the recombinant Filovirus glycoprotein, as exemplified by SEQ ID NO: 2. Where a Filovirus protein is said to lack the endogenous transmembrane domain, the entire transmembrane domain is typically absent from said glycoprotein. The term "lacking the endogenous transmembrane domain" also encompasses Filovirus glycoproteins which comprise region(s) of the endogenous transmembrane domain, but which cannot perform the function of a transmembrane domain. Methods for identifying transmembrane domain function are routine in the art.

For sequence comparison, typically one sequence acts as a reference sequence, to which test sequences may be compared. When using a sequence comparison algorithm, test and reference sequences are input into a computer, subsequent coordinates are designated, if necessary, and sequence algorithm program parameters are designated. The sequence comparison algorithm then calculates the percentage sequence identity for the test sequence(s) relative to the reference sequence, based on the designated program parameters.

Optimal alignment of sequences for comparison may be conducted, for example, by the local homology alignment algorithm of Smith and Waterman [Adv. Appl. Math. 2: 484

(1981)], by the algorithm of Needleman & Wunsch [J. Mol. Biol. 48: 443 (1970)] by the search for similarity method of Pearson & Lipman [Proc. Nat'l. Acad. Sci. USA 85: 2444 (1988)], by computer implementations of these algorithms (GAP, BESTFIT, FASTA, and TFASTA-Sequence Analysis Software Package of the Genetics Computer Group, University of Wisconsin Biotechnology Center, 1710 University Avenue, Madison, Wis. 53705), or by visual inspection [see Current Protocols in Molecular Biology, F. M. Ausbel et al, eds, Current Protocols, a joint venture between Greene Publishing Associates, In. And John Wiley & Sons, Inc. (1995 Supplement) Ausbubel].

Examples of algorithms suitable for determining percent sequence similarity are the BLAST and BLAST 2.0 algorithms [see Altschul (1990) J. Mol. Biol. 215: pp. 403-410; and "http://www.ncbi.nlm.nih.gov/" of the National Center for Biotechnology Information].

In one homology comparison, the identity exists over a region of the sequences that is at least 10 or 20 or 30 or 40 or 50 amino acid residues in length. In another homology comparison, the identity exists over a region of the sequences that is at least 60 or 70 or 80 or 90 or 100 amino acid residues in length.

An "antibody" is used in the broadest sense and specifically covers polyclonal antibodies and antibody fragments so long as they exhibit the desired biological activity. In particular, an antibody is a protein including at least one or two, heavy (H) chain variable regions (abbreviated herein as VHC), and at least one or two light (L) chain variable regions (abbreviated herein as VLC). The VHC and VLC regions can be further subdivided into regions of hypervariability, termed "complementarity determining regions" ("CDR"), interspersed with regions that are more conserved, termed "framework regions" (FR). The extent of the framework region and CDRs has been precisely defined (see, Kabat, E. A., et al. Sequences of Proteins of Immunological Interest, Fifth Edition, U.S. Department of Health and Human Services, NIH Publication No. 91-3242, 1991, and Chothia, C. et al, J. Mol. Biol. 196:901-917, 1987, which are incorporated herein by reference). Preferably, each VHC and VLC is composed of three CDRs and four FRs, arranged from amino-terminus to carboxy-terminus in the following order: FRI, CDRI, FR2, CDR2, FR3, CDR3, FR4.

The VHC or VLC chain of the antibody can further include all or part of a heavy or light chain constant region. In one embodiment, the antibody is a tetramer of two heavy immunoglobulin chains and two light immunoglobulin chains, wherein the heavy and light immunoglobulin chains are inter-connected by, e.g., disulfide bonds. The heavy chain constant region includes three domains, CHI, CH2 and CH3. The light chain constant region is comprised of one domain, CL. The variable region of the heavy and light chains contains a binding domain that interacts with an antigen. The constant regions of the antibodies typically mediate the binding of the antibody to host tissues or factors, including various cells of the immune system (e.g., effector cells) and the first component (CIq) of the classical complement system. The term "antibody" includes intact immunoglobulins of types IgA, IgG, IgE, IgD, IgM (as well as subtypes thereof), wherein the light chains of the immunoglobulin may be of types kappa or lambda.

The term antibody, as used herein, also refers to a portion of an antibody that binds to a Filovirus glycoprotein, e.g., a molecule in which one or more immunoglobulin chains is not full length, but which binds to a Filovirus glycoprotein. Examples of binding portions encompassed within the term antibody include (i) a Fab fragment, a monovalent fragment consisting of the VLC, VHC, CL and CHI domains; (ii) a F(ab')$_2$ fragment, a bivalent fragment comprising two Fab fragments linked by a disulfide bridge at the hinge region; (iii) a Fc fragment consisting of the VHC and CHI domains; (iv) a Fv fragment consisting of the VLC and VHC domains of a single arm of an antibody, (v) a dAb fragment (Ward et al, Nature 341:544-546, 1989), which consists of a VHC domain; and (vi) an isolated complementarity determining region (CDR) having sufficient framework to bind, e.g. an antigen binding portion of a variable region. An antigen binding portion of a light chain variable region and an antigen binding portion of a heavy chain variable region, e.g., the two domains of the Fv fragment, VLC and VHC, can be joined, using recombinant methods, by a synthetic linker that enables them to be made as a single protein chain in which the VLC and VHC regions pair to form monovalent molecules (known as single chain Fv (scFv); see e.g., Bird et al. (1988) Science IAl-ATi-Alβ; and Huston et al. (1988) Proc. Natl. Acad. ScL USA 85:5879-5883). Such single chain antibodies are also encompassed within the term antibody. These are obtained using conventional techniques known to those with skill in the art, and the portions are screened for utility in the same manner as are intact antibodies.

There now follows a brief description of the Figures, which illustrate aspects and/or embodiments of the present invention.

FIG. 1: Domain schematic of EBOV glycoprotein: SP, signal peptide; RBD, receptor-binding domain; mucin domain, mucin-like domain; and TM, transmembrane domain. The residue range used for the expressed sGP ectodomain construct "rGP" is indicated by the circled "START" at position 1 and the circled "STOP" at position 632.

FIG. 2: ELISA showing 50% binding titres of pooled whole ovine anti-ebola virus glycoprotein serum, sampled at time points 6, 10 and 14 weeks post primary-immunisation FIG. 3: ELISA showing 50% binding titres of ovine IgG anti-ebola virus glycoprotein, pooled from whole serum, sampled at 7 & 14 weeks post primary-immunisation.

Figure 4:
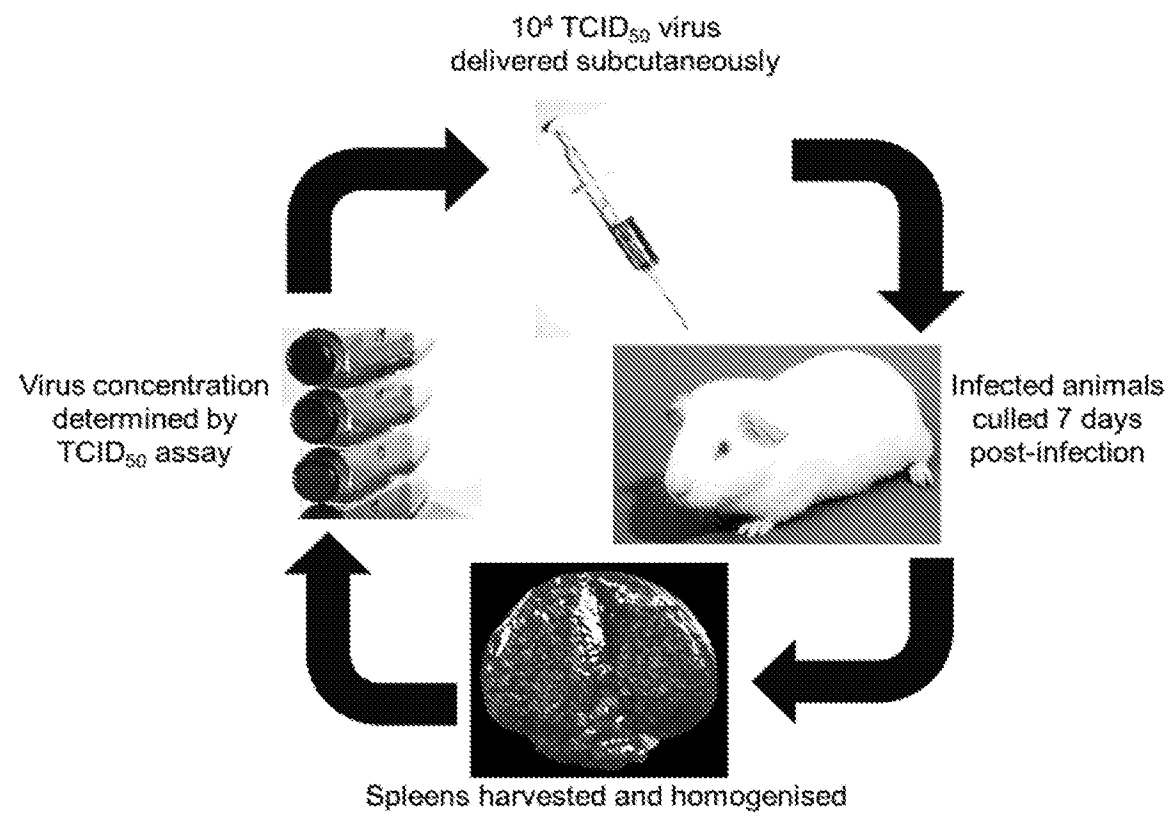

FIG. 4: Schematic representation of passaging protocol.

Figure 5:
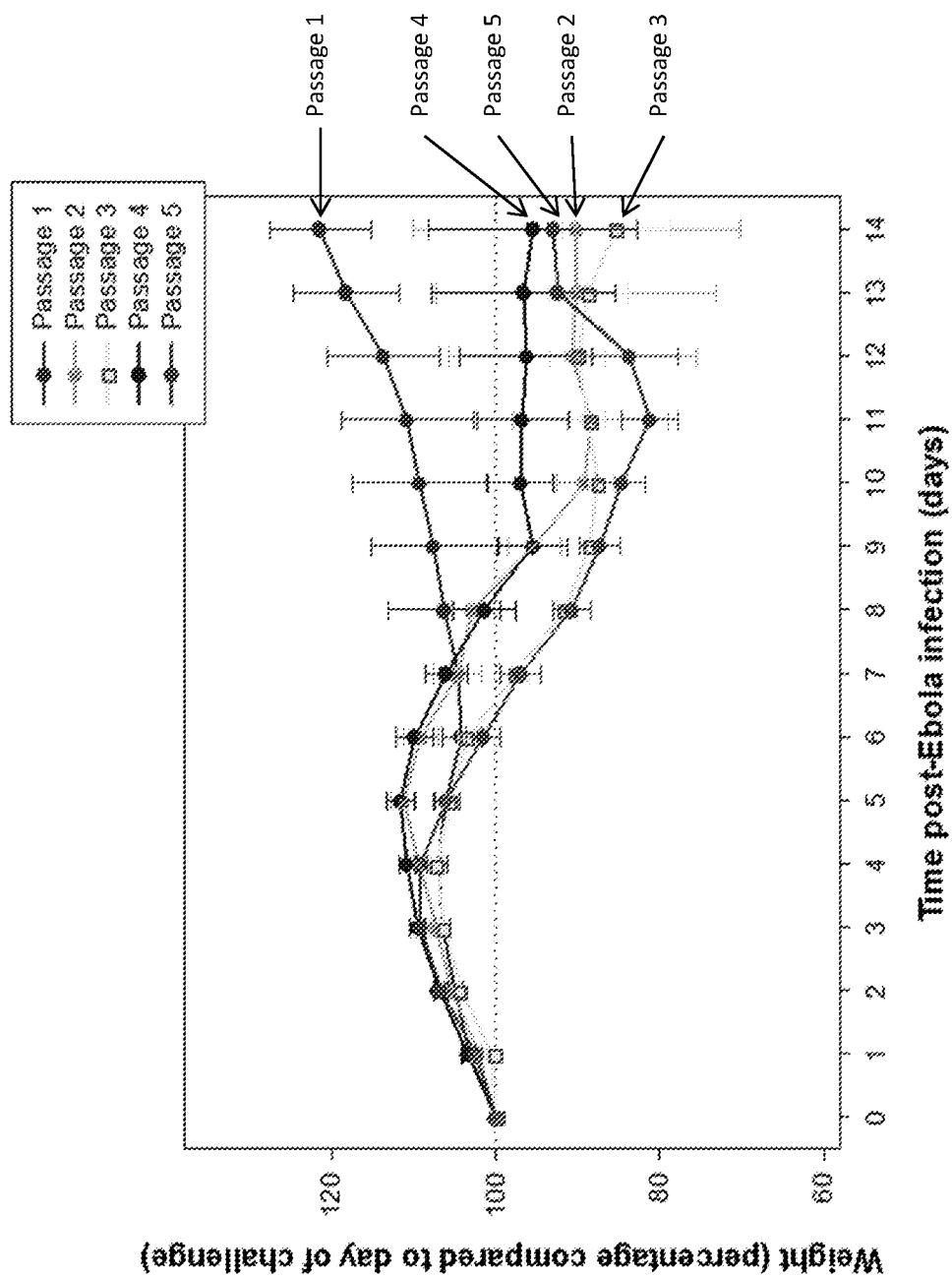

FIG. 5: Clinical data in the form of weight gain/loss and departure difference from EBOV-infected guinea pigs using virus that had been passaged from spleens harvested 7 days post infection. Weight changes compared to day of challenge, compared to control uninfected animals. Data points represent mean values from 10 animals up to day 7, and six animals up to day 14, with error bars denoting standard error.

Figure 6:
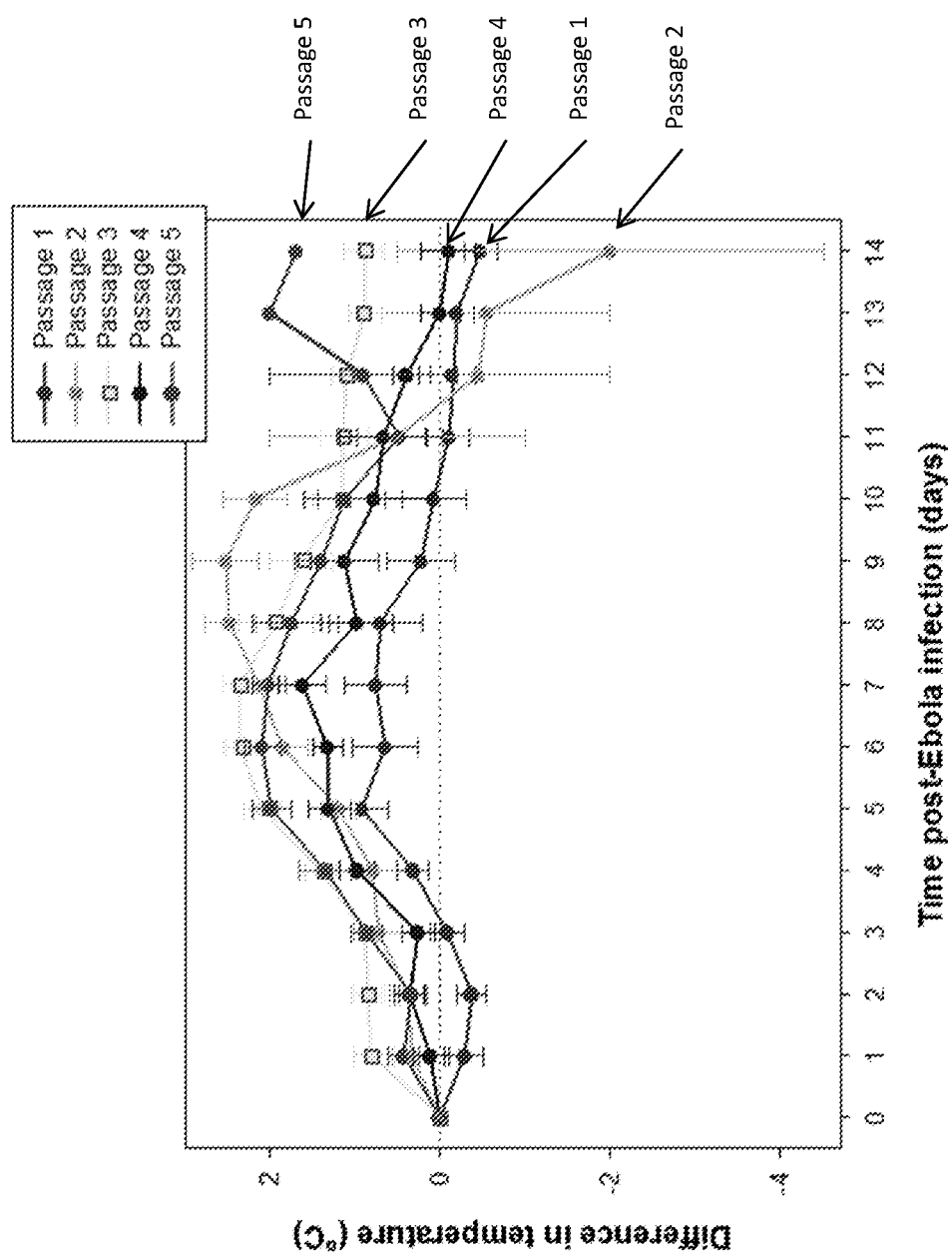

FIG. 6: Clinical data in the form of temperature difference from EBOV-infected guinea pigs using virus that had been passaged from spleens harvested 7 days post infection. Temperature changes compared to day of challenge, compared to control uninfected animals. Data points represent mean values from 10 animals up to day 7, and six animals up to day 14, with error bars denoting standard error.

Figure 7:
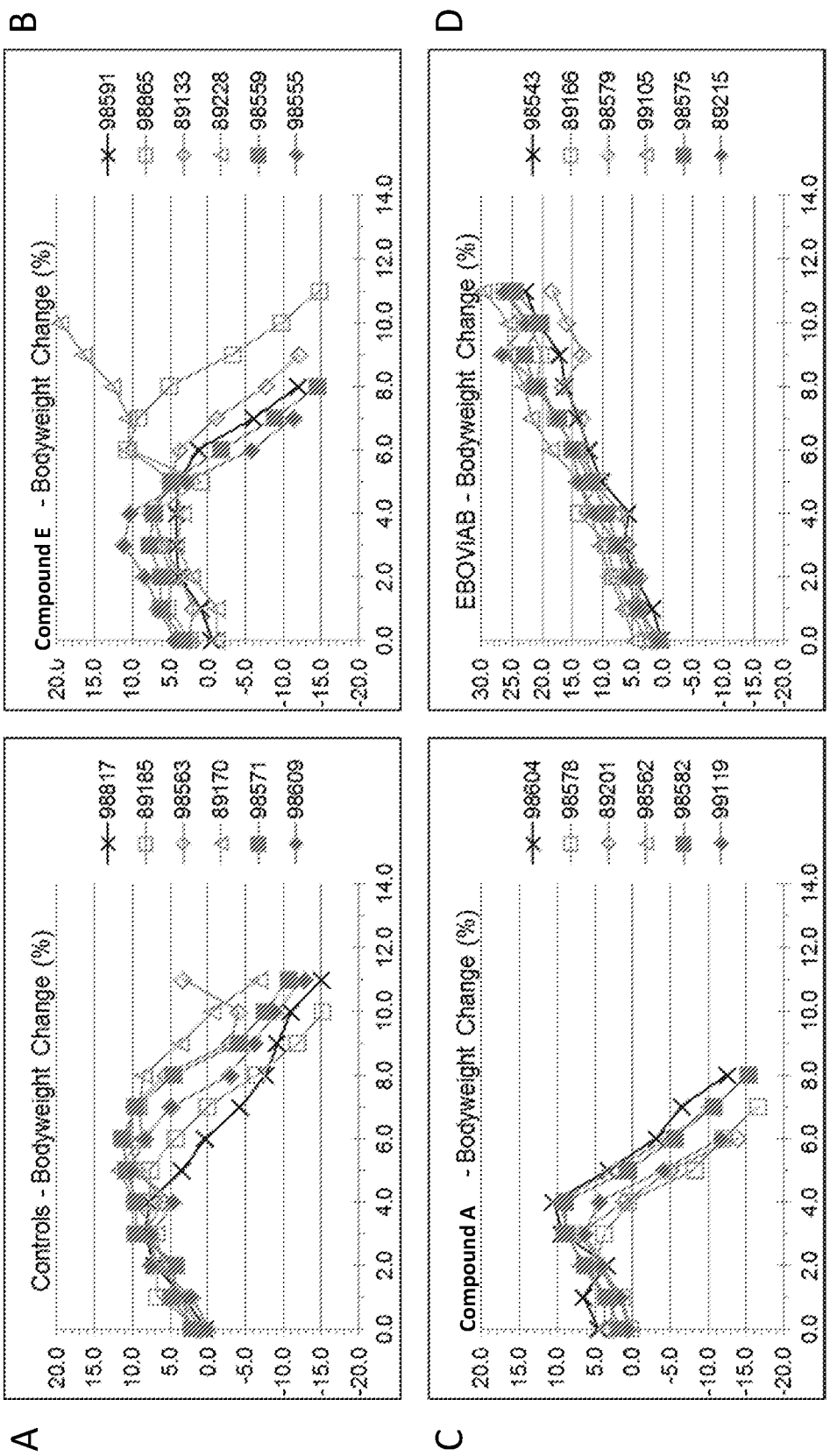

FIG. 7: Clinical data in the form of in vivo bodyweight results following challenge with EBOV. Guinea pigs were treated with (a) control, (b) compound E, (c) compound A and (d) EBOVIpAB with treatment starting 6 hours post-challenge. Curves represent bodyweight of individual Guinea pigs over time.

Figure 8:
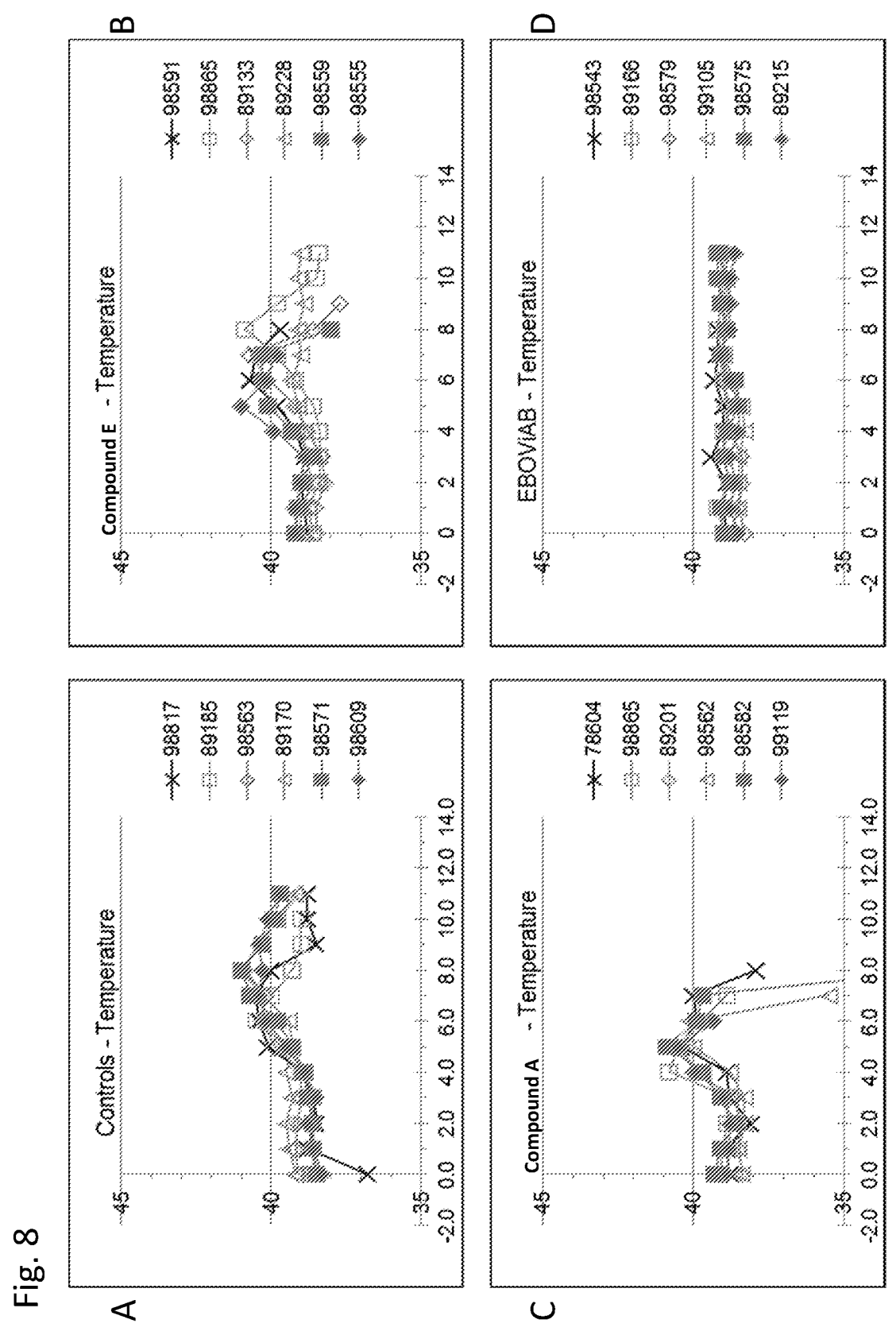

FIG. 8: Clinical data in the form of in vivo temperature results following challenge with EBOV. Guinea pigs were treated with (a) control, (b) compound E, (c) compound A and (d) EBOVIpAB with treatment starting 6 hours post-challenge. Curves represent bodyweight of individual Guinea pigs over time.

Figure 9:
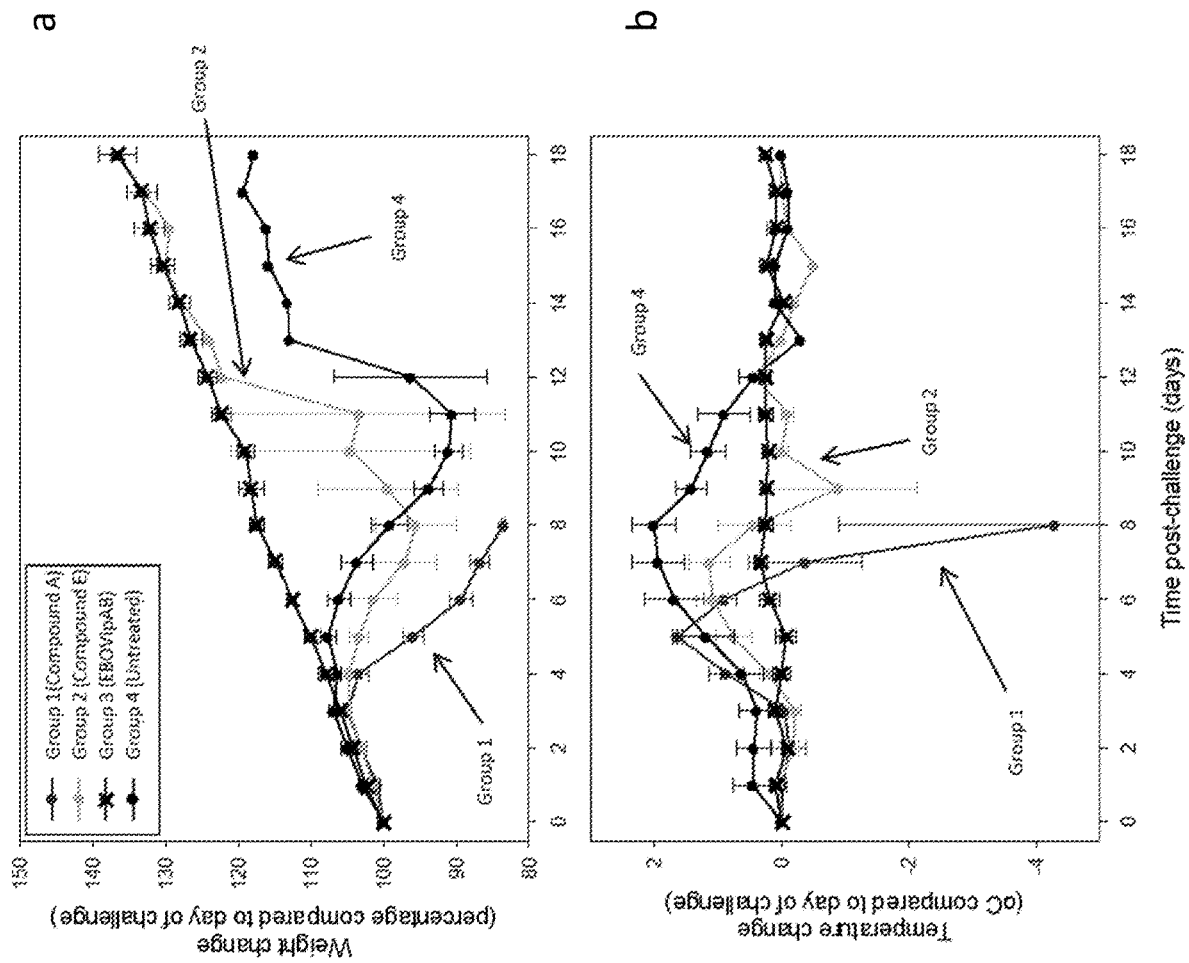

FIG. 9: Clinical data in the form of longer-term in vivo results (Guinea pigs) relating to (a) body weight; and (b) temperature, both compared to day of challenge. Guinea pigs were treated with (a) control, (b) compound E, (c) compound A and (d) EBOVIpAB with treatment starting 6 hours post-challenge.

Figure 10:
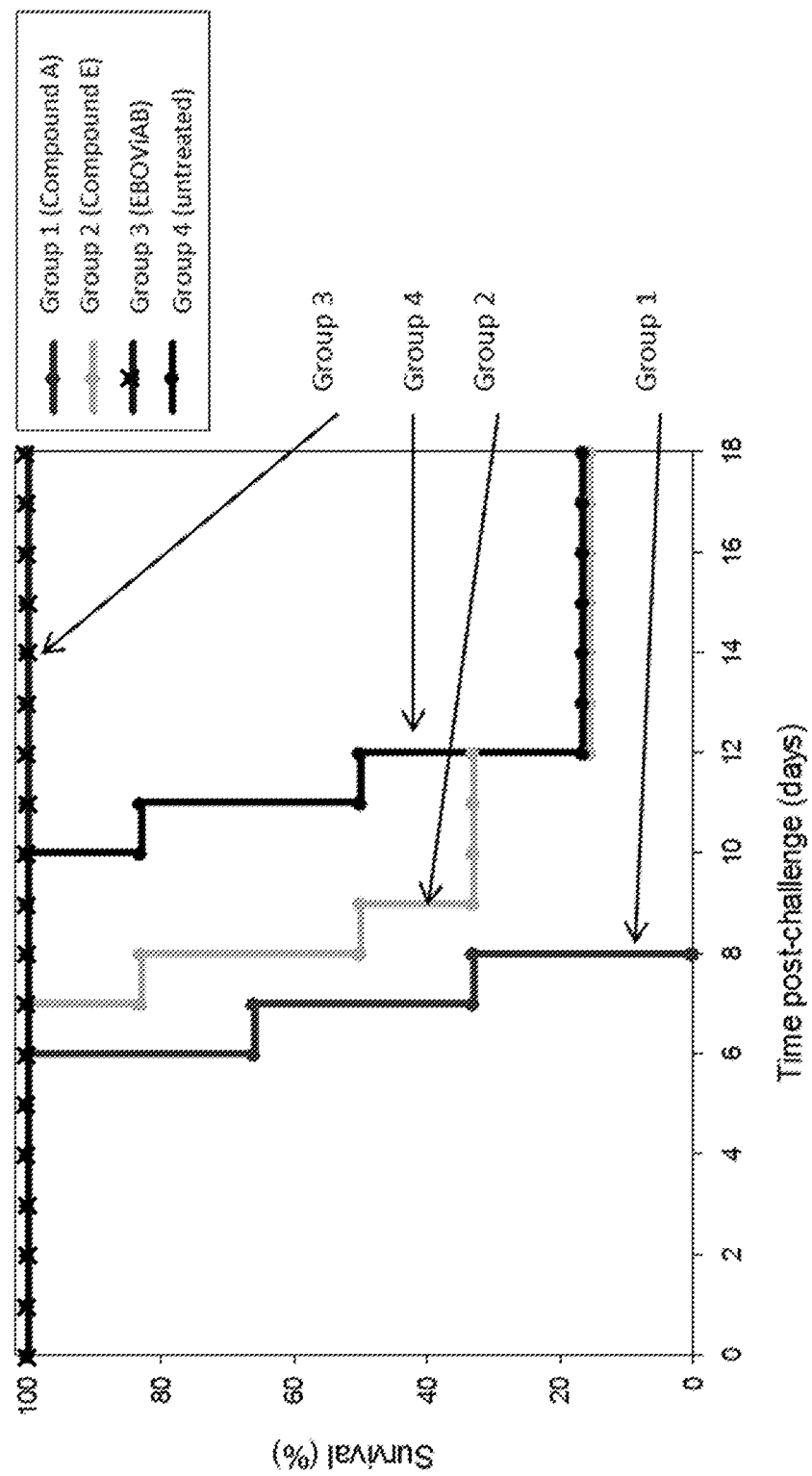

FIG. 10: In vivo survival results. Plot of % survival versus days post-challenge. Groups 1-4 (Guinea pigs) were treated with compound A, E, EBOVIpAB and controls, respectively, with treatment starting 6 hours post-challenge.

Figure 11:
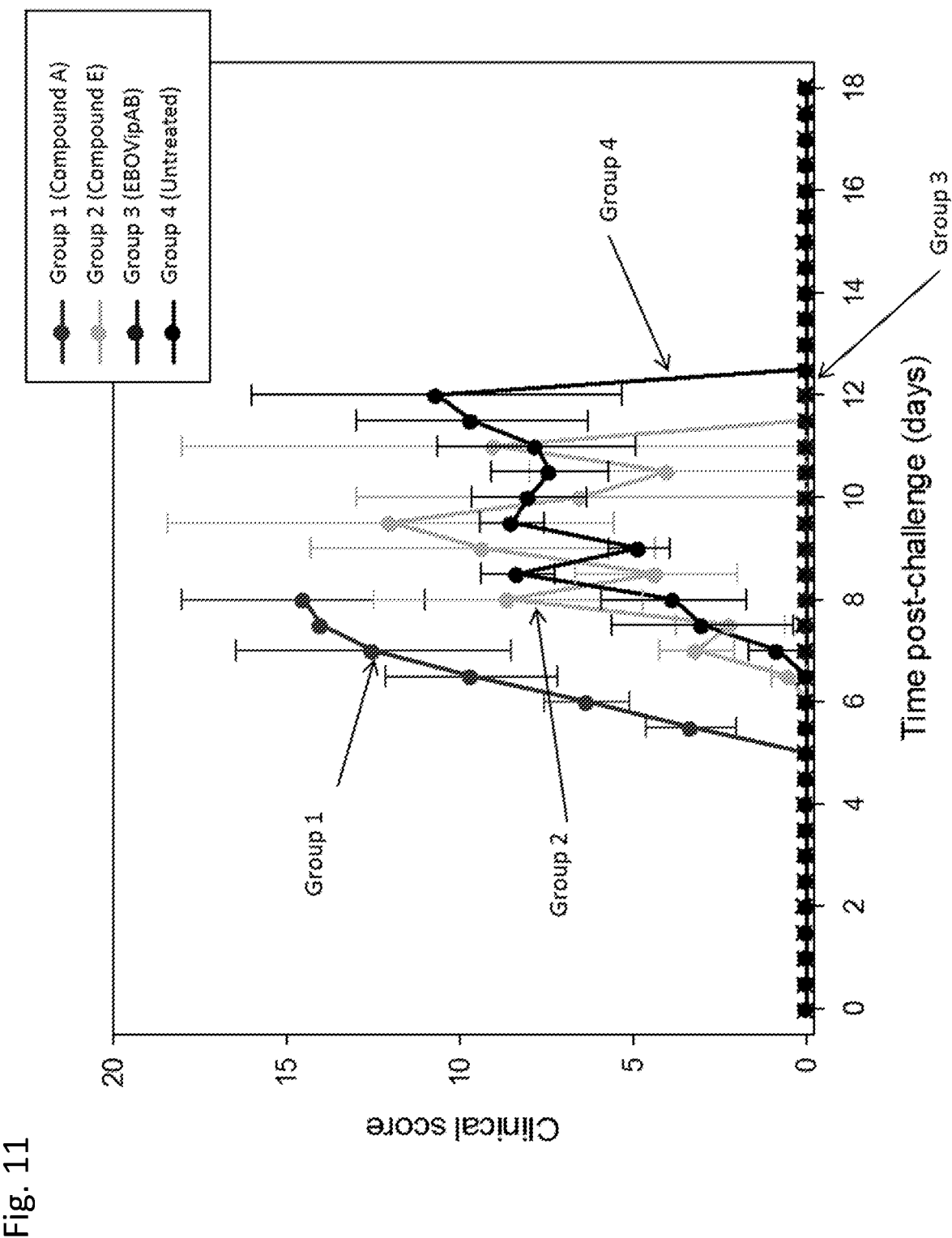

FIG. 11: In vivo clinical scores (group means with standard error). Groups 1-4 (Guinea pigs) were treated with compound A, E, EBOIpiAB and controls, respectively, with treatment starting 6 hours post-challenge.

Figure 12:
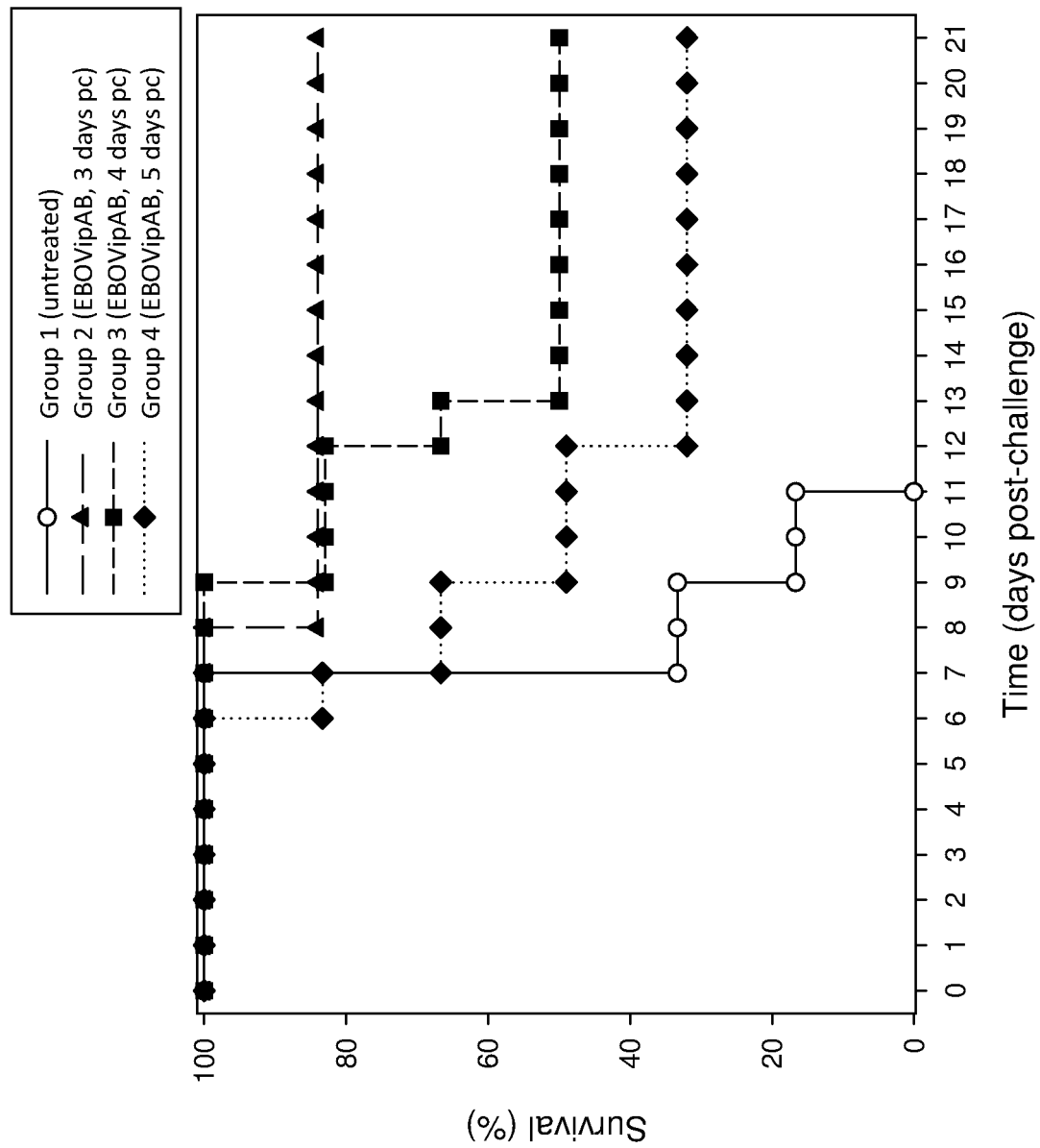

FIG. 12: Clinical data in the form of survival and clinical observations of Guinea pigs which received EBOVIpAB treatment commencing 3, 4 or 5 days after challenge with EBOV. (A) Survival analysis between EBOVIpAB treated groups compared to untreated animals. (B) Weight changes, showing percentage differences from values on the day of challenge. (C) Temperature differences in animals compared to values on the day of challenge. (D) Clinical scores of animals after challenge. In panels B-D, mean results are shown for animals still surviving in all groups, with error bars denoting standard error.

Figure 13:
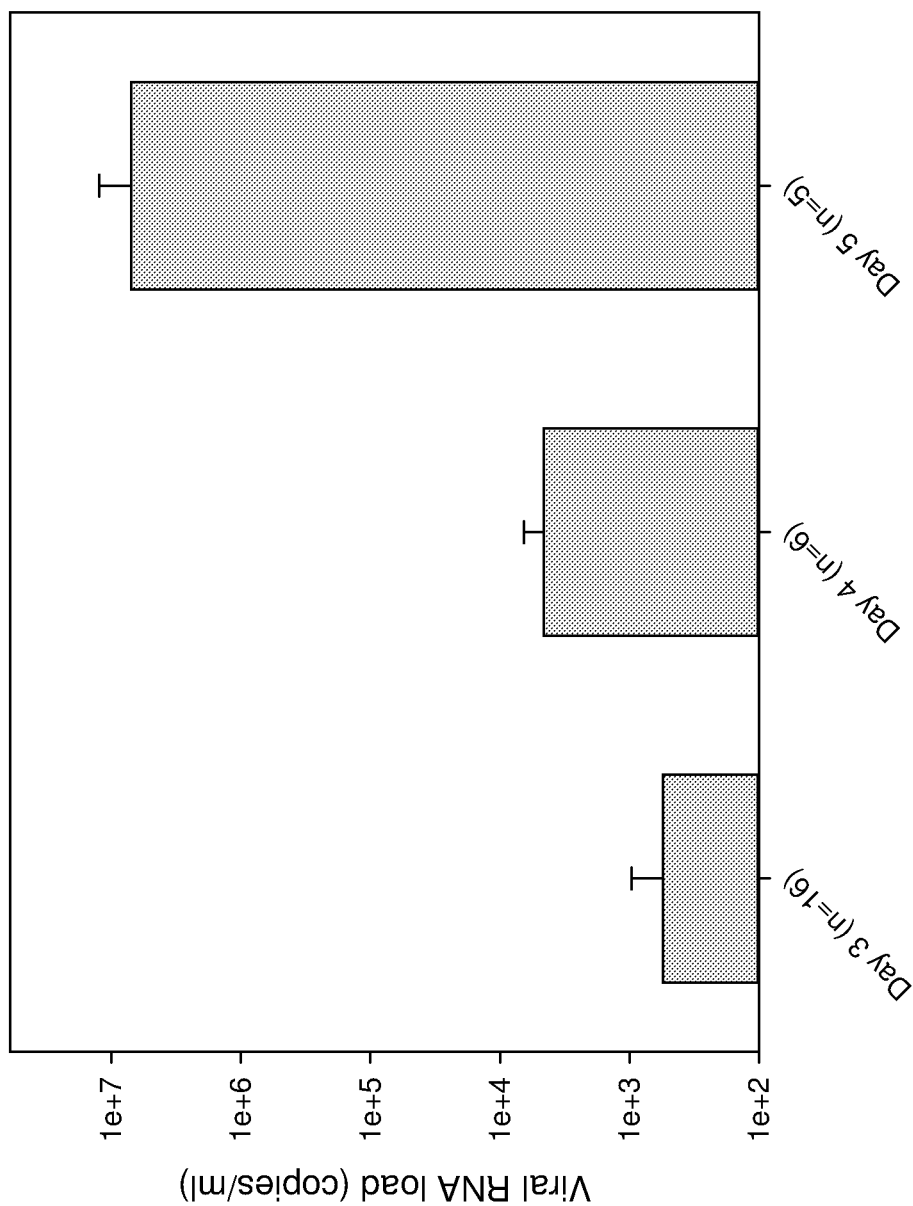

FIG. 13: EBOV viral genome copies in the blood of EBOV-challenged guinea pigs prior to administration of EBOVIpAB. Bars show mean results with error bars denoting standard error.

Figure 14:
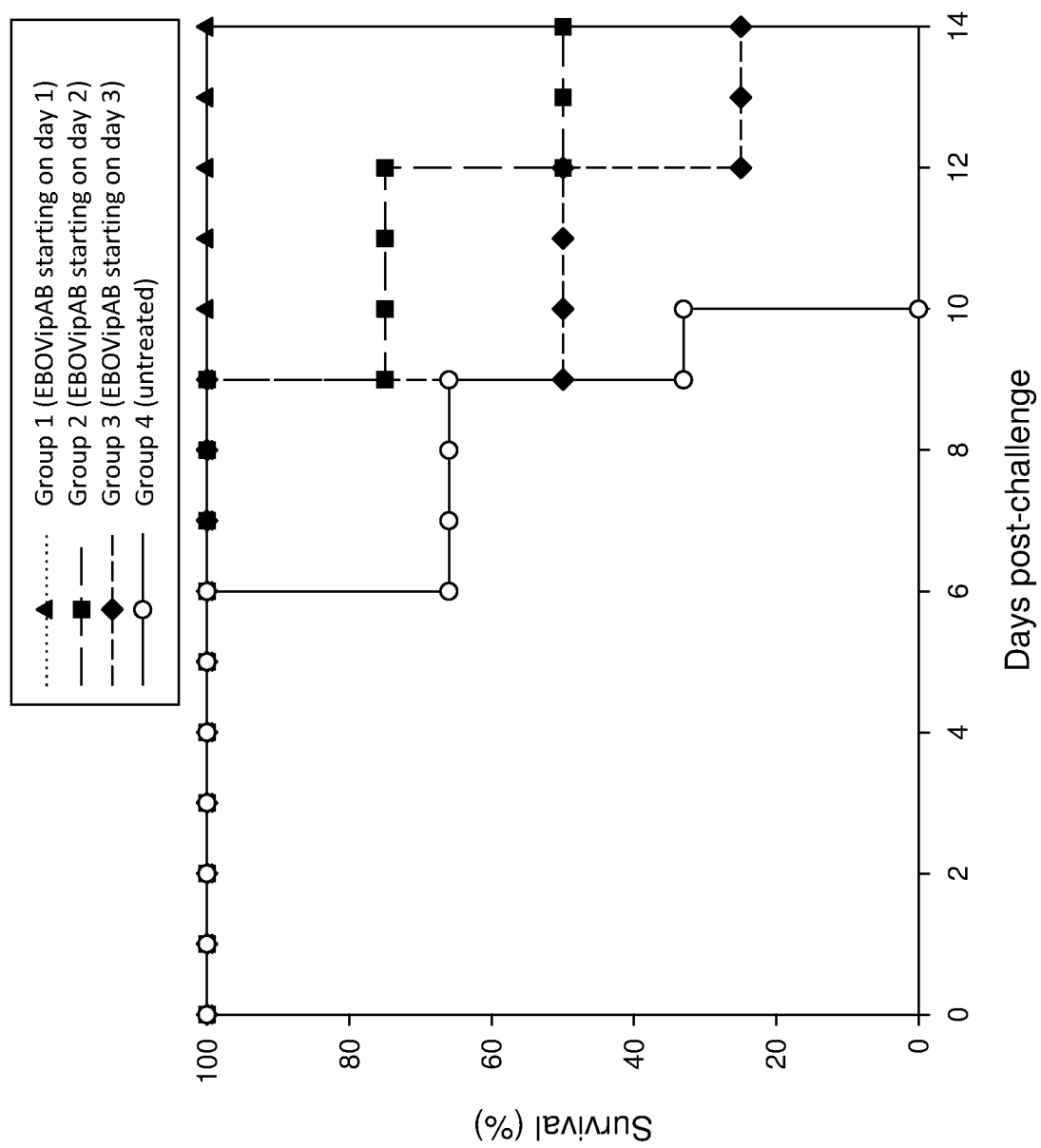

FIG. 14: Clinical data in the form of in vivo survival results in a non-human primate model. EBOV was administered at D0. "Group 1" non-human primates received daily injections of EBOVIpAB on D1-D5, D7, D9 and D11; "Group 2" non-human primates received daily injections of EBOVIpAB on D2-D6, D8, D10 and D12; "Group 3" non-human primates received daily injections of EBOVIpAB on D3-D7, D9, D11 and D13. "Group 4" non-human primates acted as an untreated control. Plot of % survival versus days post-challenge.

Figure 15:
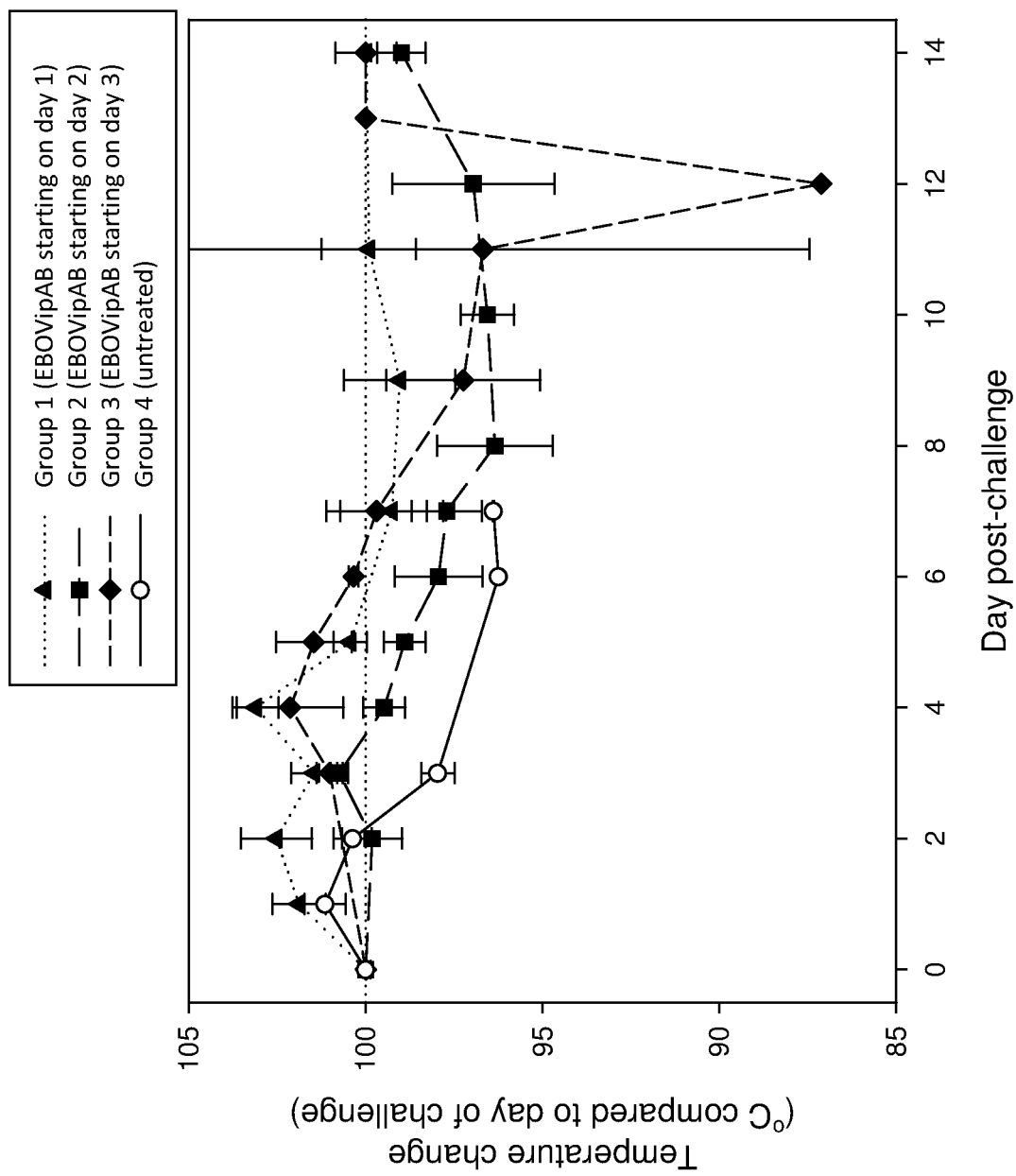

FIG. 15: Clinical data in the form of in vivo bodyweight results following challenge with EBOV in a non-human primate model. "Group 1" non-human primates received daily injections of EBOVIpAB on D1-D5, D7, D9 and D11; "Group 2" non-human primates received daily injections of EBOVIpAB on D2-D6, D8, D10 and D12; "Group 3" non-human primates received daily injections of EBOVIpAB on D3-D7, D9, D11 and D13. "Group 4" non-human primates acted as a positive control. Curves represent mean bodyweight of individual non-human primates in each group over time.

EXAMPLES

Example 1 Preparation of the EBOV Glycoprotein Antigen Lacking the Transmembrane Domain Studies were conducted with EBOV (a prototypical Filovirus) glycoprotein. The EBOV glycoprotein used to raise antibodies corresponds to the ectodomain with the transmembrane region and the membrane-proximal external region excluded—this recombinant EBOV glycoprotein corresponds to SEQ ID NO: 2, and is referred to hereinafter as "rGP". SEQ ID NO: 2 corresponds to the full length glycoprotein (SEQ ID NO: 1), with the transmembrane domain and the membrane-proximal external region omitted. Since the EBOV glycoprotein used to raise antibodies was expressed in a eukaryotic cell (detailed below), the specific the EBOV glycoprotein used to raise antibodies corresponds to 133 to D632 of SEQ ID NO: 2, because the signal peptide was cleaved by signal peptidases in the eukaryotic cell.

A schematic representation of rGP, showing the corresponding start and stop codons compared to SEQ ID NO: 1 is provided in FIG. 1.

SEQ ID NO: 5 corresponds to the nucleic acid sequence used to express rGP. SEQ ID NO: 5 was modified relative to SEQ ID NO: 4 by removal of the endonuclease site (mutation of the sequence accggt to accggc). To avoid unwanted cleavage (i.e. premature termination), the inventors inserted an 8th "A" residue into the sequence, as can be seen in SEQ ID NO: 5. As background, the native EBOV genome contains 7 consecutive A residues at this position—in 20% of cases an additional 8th A is inserted by RNA editing, leading to the production of the full-length, membrane-inserted version of the protein. SEQ ID NOs: 3 and 4 also recite 8 consecutive A residues.

To provide rGP, EBOV (prototypical Mayinga strain) DNA corresponding to the glycoprotein (SEQ ID NO: 2) was whole-gene synthesized (GeneArt), and cloned into the pHLsec vector (described by Aricescu et al. Acta Crystallogr D Biol Crystallogr. 2006 October; 62(Pt 10):1243-50). rGP was expressed with a C-terminal hexa-histidine tag. The rGP is composed of >50% oligosaccharides by weight, due the presence of N-linked glycosylation and a heavily glycosylated mucin-like domain.

Large-scale expression of rGP was performed with human embryonic kidney (HEK) 293T cells using polyethyleneimine (PEI) as the transfection reagent. HEK cells were grown to 90% confluence in Dulbecco's Modified Eagles Medium (DMEM, Sigma Aldrich, Manchester, UK) containing 10% fetal calf serum (FCS) supplemented with L-glutamine and non-essential amino acids (Invitrogen, Paisley, UK). For all transfections, a DNA to PEI mass ratio of 1:2 was used. Cells were transiently transfected in expanded surface roller bottles (Greiner Bio One, Stonehouse, UK) with 2 mg purified rGP cDNA per 1 L of 90% confluent cells. Upon transfection, the concentration of FCS was reduced to 2%. Cells were transfected in roller bottles and were incubated at 37° C.

Cell supernatant was harvested 4-5 days following transfection. Cell debris were spun down, the media sterile filtered through a 0.22 µM membrane filter and diafiltrated against a buffer containing 10 mM Tris pH 8.0, 150 mM NaCl. rGP was purified from diafiltrated supernatant by immobilised metal affinity chromatography (IMAC) using Chelating Sepharose Fast Flow $Ni^{2+}$-agarose columns (GE Healthcare, Buckinghamshire, UK). Following IMAC purification, rGP was desalted using a HiPrep 26/10 Desalting Column (GE Healthcare, Bukinghamshire, UK) against a buffer containing 10 mM Tris pH 8.0, 150 mM NaCl, concentrated, and sterile filtered for immunization. Protein purity was assessed by SDS-PAGE and Western blot analysis. High level of expression of rGP (1.5-2.5 mg/L cell culture) was obtained. Advantageously, this mammalian-expressed glycoprotein product contained authentic glycoprotein neutralising epitopes, and in sufficient quantities to induce a strong antibody response.

Example 2 Preparation of Antiserum (EBOVIpAb)

2 ml of buffer solution containing between 10 and 500 µg of rGP antigen is mixed with 2.6 ml of Freund's adjuvant. The complete form of the adjuvant is used for the primary immunisation and incomplete Freund's adjuvant for all subsequent boosts. Mixing of the adjuvant is carried out for several minutes using a mechanical device to ensure a stable emulsion. About 4.2 ml of the rGP/adjuvant mixture is used to immunise each sheep by intramuscular injection and spread across 6 sites including the neck and all the upper limbs. This is repeated every 28 days. Blood samples are taken 14 days after each immunisation. Once adequate antibody levels are achieved, larger volumes are taken (10 ml/kg body weight) into sterile bags. The bags are rotated slowly to accelerate clotting, centrifuged for 30 min at 4500×g and the serum removed under aseptic conditions and pooled. Any animal showing low titres to the desired rGP antigen is removed from the flock. This protocol provides specific antibody levels in excess of 4 g/litre of serum.

Example 3 Quantifying the Amount of Specific Antibody to rGP in Serum using Immunoaffinity Columns Column Preparation CNBr-activated Sepharose 4 Fast Flow (0.5 g dry weight) is weighed into a suitable clean container (glass or plastic). About 10 ml of diluted hydrochloric acid (1 mM) is added to swell the gel and, after 20-30 min, the gel is transferred to a 10-mL glass column and washed with a further 20 mL of HCl (1 mM), followed by 20 mL of coupling buffer (sodium bicarbonate, 100 mM, pH 8.3, containing 500 mM sodium chloride). rGP solution (1 mL) at a concentration of 1 mg/mL is diluted to 5 mL with coupling buffer and added to the column containing the activated gel and the contents mixed gently until the gel is re-suspended and rotated at room temperature overnight (16-18 hr). The column is then drained and 5 ml of blocking reagent (ethanolamine solution, 1M) added, mixed gently and rotated for 2 hr at room temperature. Next, the column is washed with 20 mL coupling buffer followed by 20 mL of elution buffer (glycine solution 100 mM, pH 2.5). This step is repeated twice. The column is finally washed with 20 mL of assay buffer (sodium phosphate buffer, 10 mM, pH 7.4 containing 500 mM sodium chloride and sodium azide at a final concentration of 1 g/L) and stored in 3-5 mL of assay buffer at 2-8° C. until used.

Column Assessment

The specific binding and non-specific capacity of the column is typically assessed prior to use. The column is removed from the refrigerator and allowed to equilibrate to room temperature and then washed with 25 mL of assay buffer. Increasing volumes of the product (whole antisera, purified IgG, Fab or F(ab')$_2$) are individually loaded onto the column and mixed end-over-end gently for 1 hr at room temperate. The unbound fraction is washed off with 25 mL of assay buffer and the bound fraction then eluted from the column with 20 ml of elution buffer (glycine buffer 100 mM, pH 2.5). The protein content of the eluted fraction is determined spectrophotometrically at 280 nm using an extinction coefficient relevant to the product namely 1.5 for sheep IgG (Curd et al., 1971) or 1.4 for sheep Fab and F(ab')$_2$ (Allen, 1996). A saturation curve is obtained by plotting the amount of eluted protein against the volume loaded.

Affinity Column for Product Assessment

The column is used for GMP/GLP assessment of in-process and final product viz whole antisera, purified IgG, Fab and F(ab')$_2$. It is also used to assess and monitor the immune response of the immunised animals.

Figure 3:
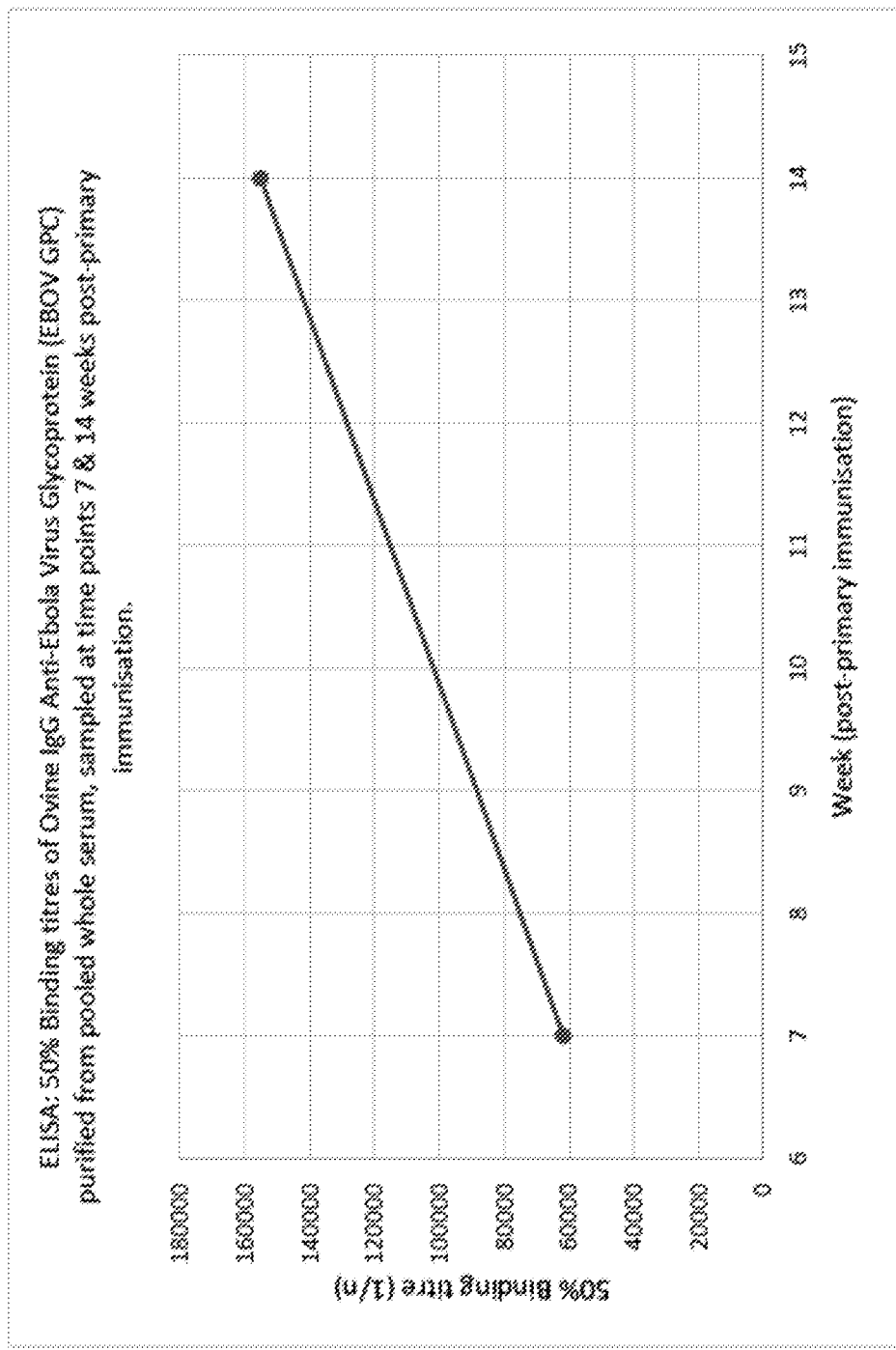

The column is removed from the refrigerator and allowed to equilibrate to room temperature when it is washed with 25 mL of assay buffer. Product (1 mL) is added to the column and mixed end-over-end gently for 1 hr at room temperature following which the unbound fraction is washed off with 25 mL of assay buffer (sodium phosphate buffer, 10 mM, pH 7.4 containing 500 mM sodium chloride and sodium azide at a final concentration of 1 g/L). The bound fraction is then eluted with 20 ml of elution buffer (glycine buffer 100 mM, pH 2.5) and its protein content determined spectrophotometrically at 280 nm using an extinction coefficient relevant to the product. FIG. 2 shows the binding analysis of pooled whole serum from sheep immunised with rGP. FIG. 3 shows the binding analysis of IgG purified from pooled whole serum from sheep immunised with rGP.

Example 4 In Vitro Screening of Candidate Compounds

To achieve rapid down-selection of experimental therapies for EBOD, the inventors performed an in vitro screen of 20 candidate compounds, which were identified according to their Technology Readiness Score, their availability to make a difference to the current epidemic, and their likely efficacy against EBOV. EBOVIpAb was included in the screen. The effects of these 20 compounds on cells (toxicity) and viral amplification was assessed using MRC-5 and VeroE6 cells.

Example 5 In Vitro Assessment of Compounds

Cells were assessed according to Ct differential, as a measure of change in viral load, and also cell appearance. A Ct differential of >2.9 corresponds to a 10-fold reduction. The results of the in vitro screen are provided in Table 2.

TABLE 2

Ct and Cell appearance results.

| | MRC-5 | | VeroE6 | |
|---|---|---|---|---|
| Compound | Ct difference | Cell appearance | Ct difference | Cell appearance |
| 1 Compound A | *2.9* | | *-6.8* | |
| 2 EBOVIpAb | 2.3 | ✓ (CPE) | *-4.5* | ✓ |
| 3 Compound C | *3.7* | | *-3.5* | |
| 4 Compound D | 4.5 | | -0.4 | |
| 5 Compound E | *3.7* | ✓ | 1.8 | ✓ |
| 6 Compound F | -2.1 | ✓ | *-5.9* | ✓ |
| 7 Compound G | -0.8 | | 2.6 | |
| 8 Compound H | 0.5 | | 2.0 | |
| 9 Compound I | 2.5 | | *3.6* | |
| 10 Compound J | *-3.1* | ✓ | *-4.5* | ✓ |
| 11 Compound K | *>10* | ? | *7.2* | ? |
| 12 Compound L | *>10* | ? | *>10* | ? |
| 15 Compound O | *-3.1* | ✓ | *-2.5* | ✓ |
| 16 Compound P | *-3.7* | ✓ | *-8.0* | ✓ |
| 17 Compound Q | -1.5 | ✓ | *-2.9* | ✓ |
| 18 Compound R | *-3.9* | ✓ | *-4.4* | ✓ |
| 19 Compound S | -1.8 | ✓ | *-4.0* | ✓ |
| 20 Compound T | *-2.9* | ✓ | *-4.5* | ✓ |
| 21 Compound U | -1.8 | ✓ | -0.5 | ✓ |
| 22 Compound V | *3.4* | | -0.3 | ✓ |

Ct values of >2.9 (10-fold reduction)in italics and bold font.
"CPE" means cytopathic effect observed.
Preferred compounds are indicated by asterisks.

The lower dilutions of the compounds which showed activity were analysed to determine whether a dose response was evident (see Table 3).

TABLE 3

Analysis of lower dilutions of the compounds to determine whether a dose response was evident.

| Number | Name | Activity ($S_{Ct}$) |
|---|---|---|
| 1 | Compound A | 4.7 uM-2 Ct |
| 2 | EBOVIpAb | 1:32 = 1 Ct* |
| 3 | Compound C | No data |
| 4 | Compound D | >0.5 μm |
| 5 | Compound E | 3 μM = 1.8- 3.7 Ct |
| 7 | Compound F | >10 μM |
| 8 | Compound H | >7.5 μM |
| 9 | Compound I | >2 μM |
| 11 | Compound K | 20 μg/ml = 5 Ct |
| 12 | Compound L | >10 mg/ml |
| 22 | Compound V | >2 μM |

Ct values of >2.9 (10-fold reduction) in italics and bold font.

To help identify a shortlist of candidate compounds, the inventors assessed the Ct scores and cell appearance at different compound dilutions (Table 4).

TABLE 4

Detailed assessment of Ct scores cell appearance. Ct values of >2.9 (10-fold reduction) in italics and bold font.

| | | | MRC-5 | | VeroE6 | |
|---|---|---|---|---|---|---|
| No. | Compound | Dilution | Ct difference | Cell appearance | Ct difference | Cell appearance |
| 1 | *Compound A* | 1x | 2.9 | | -6.7 | |
| | | 0.1x | 2.1 | ✓ | -8.6 | ✓ |
| | | 0.02x | 1.0 | ✓ | -1.6 | ✓ |
| 2 | *EBOVIpAb* | 1:8 | 2.3 | ✓ (CPE) | -4.5 | ✓ |
| | | 1:16 | 2.4 | ✓ (CPE) | -0.8 | ✓ |
| | | 1:32 | 2.2 | ✓ (CPE) | 1.1 | ✓ |
| 3 | Compound C | 1x | 3.7 | | -3.5 | |
| | | 0.1x | 3.3 | | -0.8 | |
| | | 0.02x | 3.8 | | 1.2 | |
| 4 | Compound D | 1x | 4.5 | | -0.4 | |
| | | 0.1x | 4.0 | | -0.7 | |
| | | 0.02x | 3.8 | | -1.4 | ✓ |
| 5 | *Compound E* | 1x | 3.7 | ✓ | 1.8 | ✓ |
| | | 0.1x | 0.9 | ✓ | 2.2 | ✓ |
| | | 0.02x | -0.2 | ✓ | 2.7 | ✓ |
| 7 | Compound G | 1x | 0.8 | | 2.6 | |
| | | 0.1x | -1.9 | ✓ | -1.0 | ✓ |
| | | 0.02x | -2.1 | ✓ | -0.7 | ✓ |
| 8 | Compound H | 1x | 0.5 | | 2.0 | |
| | | 0.1x | -3.9 | ✓ | -4.5 | ✓ |
| | | 0.02x | -3.3 | ✓ | -3.2 | ✓ |
| 9 | Compound I | 1x | 2.5 | | 3.6 | |
| | | 0.1x | -0.9 | ✓ | -1.6 | ✓ |
| | | 0.02x | -1.6 | ✓ | -1.5 | ✓ |
| 11 | Compound K | 1x | >10 | ? | 7.2 | ? |
| | | 0.1x | 6.6 | ? | 4.6 | ? |
| | | 0.02x | 5.2 | ? | 1.7 | ? |
| 12 | Compound L | 1x | >10 | ? | >10 | ? |
| | | 0.1x | 7.0 | ? | 3.8 | ? |
| | | 0.02x | 5.6 | ? | 5.4 | ? |
| 22 | Compound V | 1x | 3.4 | | -0.3 | |
| | | 0.1x | -1.1 | ✓ | -2.4 | ✓ |
| | | 0.02x | -2.2 | ✓ | -3.7 | ✓ |

"CPE" means cytopathic effect observed. Preferred compounds are indicated by asterisks.

The in vitro screening provided a refined list of Compound A, EBOVIpAb and Compound E for in vivo studies.

Example 6 In Vivo Forced Evolution of EBOV

A forced evolution model was used to increase EBOV pathogenicity in guinea pigs [Dowall et al. (2014) Genome Biology 15:540]]. EBOV was sequentially passaged in vivo using a guinea pig model of infection. EBOV is initially non-pathogenic in guinea pigs, but becomes more virulent and adapted to replicating in this host.

In more detail, Guinea pigs were infected with EBOV (ME718 strain) and the virus was serially passaged to develop uniform lethality in guinea pigs (FIG. 4).

There were 10 guinea pigs per passage. Four animals were used for the preparation of spleen homogenate for subsequent virus infection (culled 7 days post challenge) and six were taken forward for measuring survival rates and clinical parameters (for up to 14 days post challenge). Adaptation of EBOV to growth in the guinea pigs was achieved with serial passage involving a subcutaneous injection of $10^4$ TCID$_{50}$ EBOV, with spleens harvested 7 days post infection (as a source of progeny virus). Virus titre was determined and a new inoculum prepared before administering $10^4$ TCID$_{50}$ EBOV to a new group of guinea pigs. This was repeated until there was clinical and virological evidence that the virus adapted to the guinea pig host. Animals were observed for 2 weeks post infection. Weight data indicated that guinea pigs showed a minimal response to the initial challenge, whereas with subsequent passages weight loss exceeding 10% was observed (FIG. 5).

Similarly, with temperatures the same responses were observed, where only after initial passage in the guinea pigs were temperature increases of between 1° C. and 2.5° C. observed (FIG. 6).

At passage two several animals that met humane clinical endpoints displayed symptoms of hypothermia prior to being euthanised. Hypothermia has been previously observed in Rhesus macaques experimentally infected with EBOV via the aerosol route. Six animals from each passage study that were scheduled to last 14 days post infection were used to assess mortality. By five passages, 75% mortality was observed with a challenge dose of $10^4$ $TCID_{50}$. There was also no increase in viral titre in the spleen collected from animals culled at day 7 (Table 5) compared with the previous passage, indicating that the viral burden had peaked. The minimum lethal dose of the passaged virus was determined to be $10^3$ $TCID_{50}$ (data not shown).

TABLE 5

Virus titre from spleen preparations following passaging

| | Virus titre from spleen preparation ($TCID_{50}$) |
|---|---|
| Passage 1 | $2.1 \times 10^4$/spleen |
| Passage 2 | $3.0 \times 10^7$/spleen |
| Passage 3 | $5.8 \times 10^7$/spleen |
| Passage 4 | $6.1 \times 10^7$/spleen |
| Passage 5 | $6.1 \times 10^7$/spleen |

The titre of EBOV in the spleens isolated from four guinea pigs taken from each passage increased, and then reached a plateau indicating that the virus had become adapted to grow in the guinea pig model This method of adapting EBOV has been used by others and mortality was first shown to occur during passages three to four. Complete lethality was then detected soon after, but ranged from passage four to seven. While 50% lethality was seen in the second passage in the current study, this was most likely due to the low titres in the passage one material requiring a higher concentration of spleen homogenate to be delivered to the guinea pigs in order to achieve challenge with $10^4$ $TCID_{50}$. This amount of material would have had adverse impacts due to lipid peroxidation, and protein oxidation and pro-apoptotic factors through cellular damage during preparation of the homogenate.

Example 7 In Vivo Evaluation of Lead Compounds

Guinea pigs (approx. 300 g) were supplied with vascular catheter. Animals challenged (sc) with Ebola virus (Zaire strain) at a dose of $10^3$ $TCID_{50}$ per 0.2 ml. Animals were treated with the respective compound 6 hours after administration of EBOV. In vivo protocol summaries are provided in Tables 6 and 7.

TABLE 6

Summary of in vivo test compounds

| Test compound | Mechanism | Dose/route |
|---|---|---|
| Compound A | | 33.75 mg/kg oral (1 ml) 2x daily |
| Compound E | Small molecule inhibitor | 44 mg/kg oral (1 ml) 2x daily |
| EBOVIpAb (Micropharm) | Ovine IgG | 500 µl of approx. 50 mg/ml solution, iv every 3 days |

TABLE 7

Summary of in vivo study

| Day | Activity |
|---|---|
| Day 0 | Challenge<br>Monitor<br>Administer test compounds |
| Days 1-14 | Administration of test compounds<br>Weight and temperature monitored<br>Clinical observations |
| Day 8 | Remove 0.5 ml blood via catheter<br>RNA |
| Day 14 | Cull survivors<br>Necropsy (liver/spleen)<br>Samples for RNA, viral loads |

Body Weight Analysis

As shown in FIG. 7, Guinea pigs treated with control compound continued to gain weight until ~day 3, at which point weight began to plateaux. At ~day 6, control bodyweights were observed to decrease rapidly. With the exception of one Guinea pig (89228), Compound E also appeared to accelerate the decrease in bodyweight, compared to controls. Compound A appeared to accelerate the decrease in bodyweight, compared to controls, with a rapid loss of bodyweight at a ~day 4.

Surprisingly, Guinea pigs treated with EBOVIpAb continued to gain weight at a consistent rate, even at the endpoint of the experiment, even at day 18 post-challenge (see FIG. 9a). This is particularly surprising in view of the highly stringent assay conditions, in which Guinea pigs were challenged 6 hours prior to treatment with EBOV.

Body Temperature Analysis

As shown in FIG. 8, Guinea pigs treated with control compound experienced an increase in body temperature from ~day 4. Body temperatures peaked at ~days 7-9, after which body temperatures decreased to levels slightly higher than that at time zero. Similar results were observed in Compound E-treated Guinea pigs, whereas Compound A appeared to accelerate the increase in body temperature, at ~day 3-4. However, this is likely due to the effect of oral gavage on food intake.

Surprisingly, Guinea pigs treated with EBOVIpAb showed no increase in body temperature throughout the entire duration of the experiment, even at day 18 post-challenge (see FIG. 9b). As noted above, this is particularly surprising in view of the stringent assay conditions, in which Guinea pigs were challenged 6 hours prior to treatment with EBOVIpAb.

Mortality Analysis

As shown in FIG. 10, EBOV treatment of Guinea pig controls proved fatal at ~day 10. Compound A appeared to accelerate time to death, however, oral gavage twice daily likely exacerbated clinical symptoms with bleeding from upper GI tract and disrupted food intake. Compound E again appeared to a lesser extent, accelerate time to death, and inventors propose that the delivery-route may have contributed to this effect. Inventors note that there were individual improvements in the Compound E-treated Guinea pigs.

Surprisingly, all of the Guinea pigs treated with EBOVIpAb survived challenge with EBOV, even at the endpoint of the experiment. As noted above, this is particularly surprising in view of the highly stringent assay conditions, in which Guinea pigs were challenged 6 hours prior to treatment with EBOVIpAb.

Clinical Analysis

FIG. 11 shows clinical scores of Guinea pigs following treatment with EBOV. Clinical scores were calculated according to signs, which were assigned a numerical value, as shown in Table 8:

TABLE 8

Signs recorded were assigned a numerical value

| Sign | Score |
| --- | --- |
| Normal | 0 |
| Ruffled fur | 2 |
| Lethargy | 3 |
| Bloated | 3 |
| Pinched | 3 |
| Dehydrated | 3 |
| Hunched | 3 |
| Wasp wasted | 3 |
| Laboured breathing | 5 |
| Rapid breathing | 5 |
| Inactive | 5 |
| Immobile | 10 |

Administration of compound A led to a rapid increase in clinical score. Compound E again appeared to a lesser extent, to increase clinical scores, similar to controls.

Surprisingly, the Guinea pigs treated with EBOVIpAb exhibited no clinical scores, even at the endpoint of the experiment.

In conclusion, treatment with EBOVIpAb provided drastic improvements compared to controls. Surprisingly, treatment with EBOVIpAb resulted in no symptoms of EBOV, measured either by weight loss, temp increase or death, and zero clinical score.

Example 9 In Vivo Evaluation of EBOVIpAb Administered Post-challenge with EBOV (Guinea Pig Model)

Efficacy of EBOVIpAb Treatment Beginning 3, 4 or 5 Days Post-EBOV Challenge.

EBOVIpAb was first delivered to Guinea pigs 3, 4 or 5 days after infection with a lethal dose of EBOV, (corresponding to Groups 2-4, respectively). Group 2 received 0.5 ml (51 mg/ml) EBOVIpAb twice per day on days 3, 4, 5, 7, 9 and 10 post-challenge. Groups 3 and 4 received a similar EBOVIpAb dosage regime commencing 4 or 5 days after EBOV challenge, respectively.

Mortality analysis showed that all untreated animals (Group 1, positive controls) met humane endpoints by day 11 (FIG. 12A). Surprisingly, EBOVIpAb treatment commencing 3, 4 or 5 days after challenge provided 83.3%, 50% and 33% survival respectively, representing a marked improvement over untreated positive controls. This is particularly surprising in view of the highly stringent assay conditions, in which Guinea pigs were shown to possess a high viral load at the time of EBOVIpAb administration (see Table 13, discussed below).

Figure 12B:
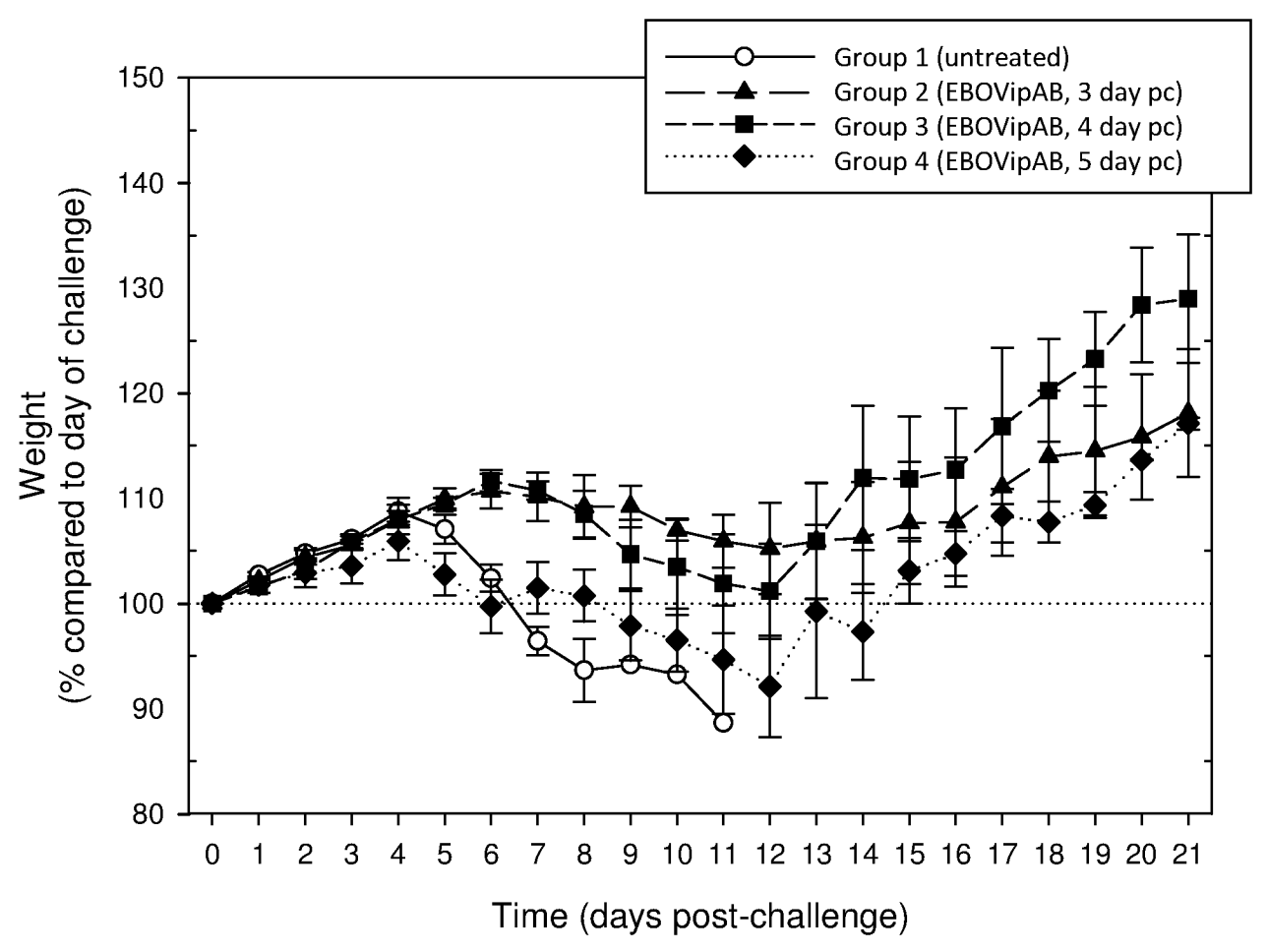
Figure 12C:
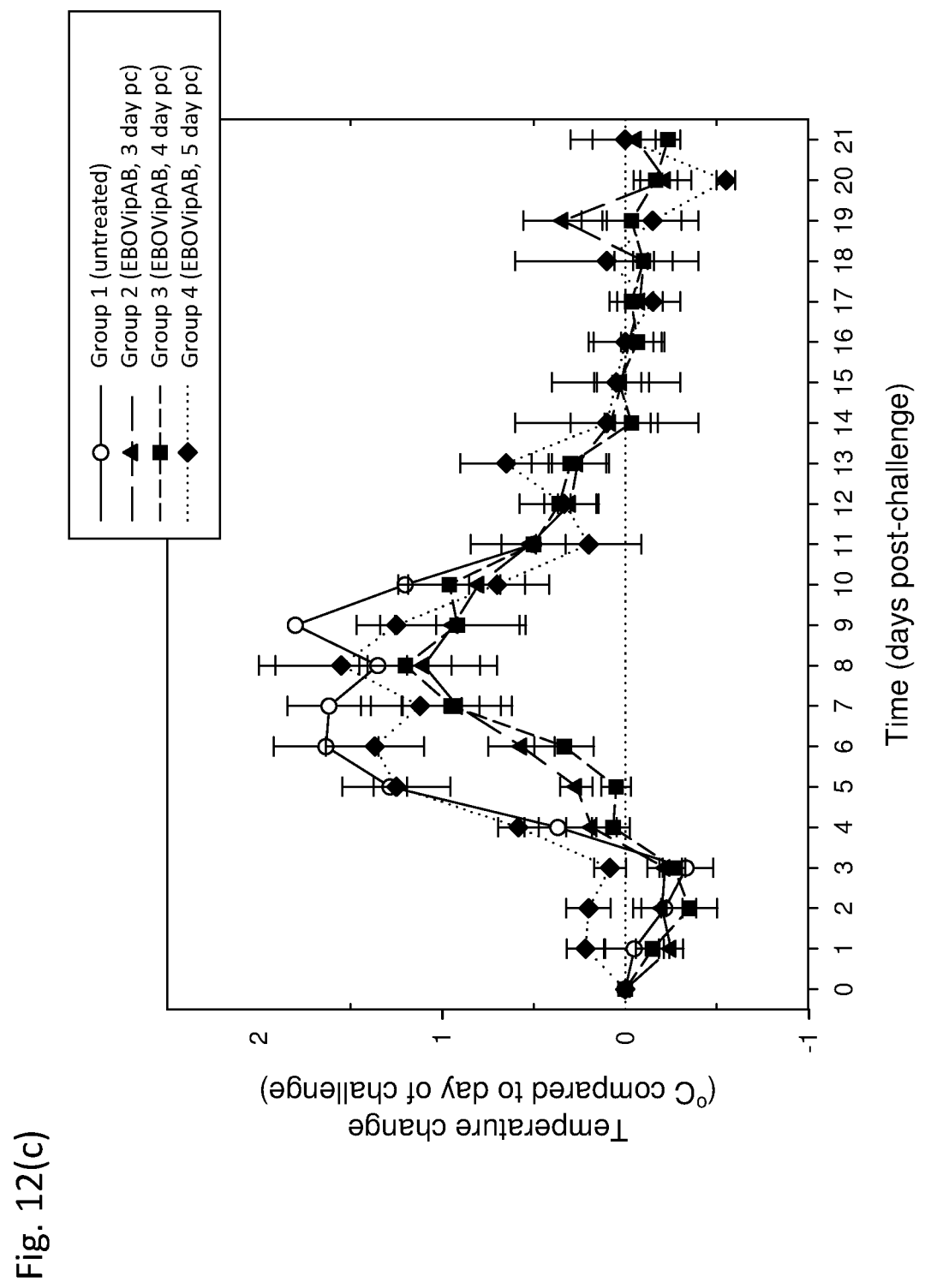
Figure 12D:
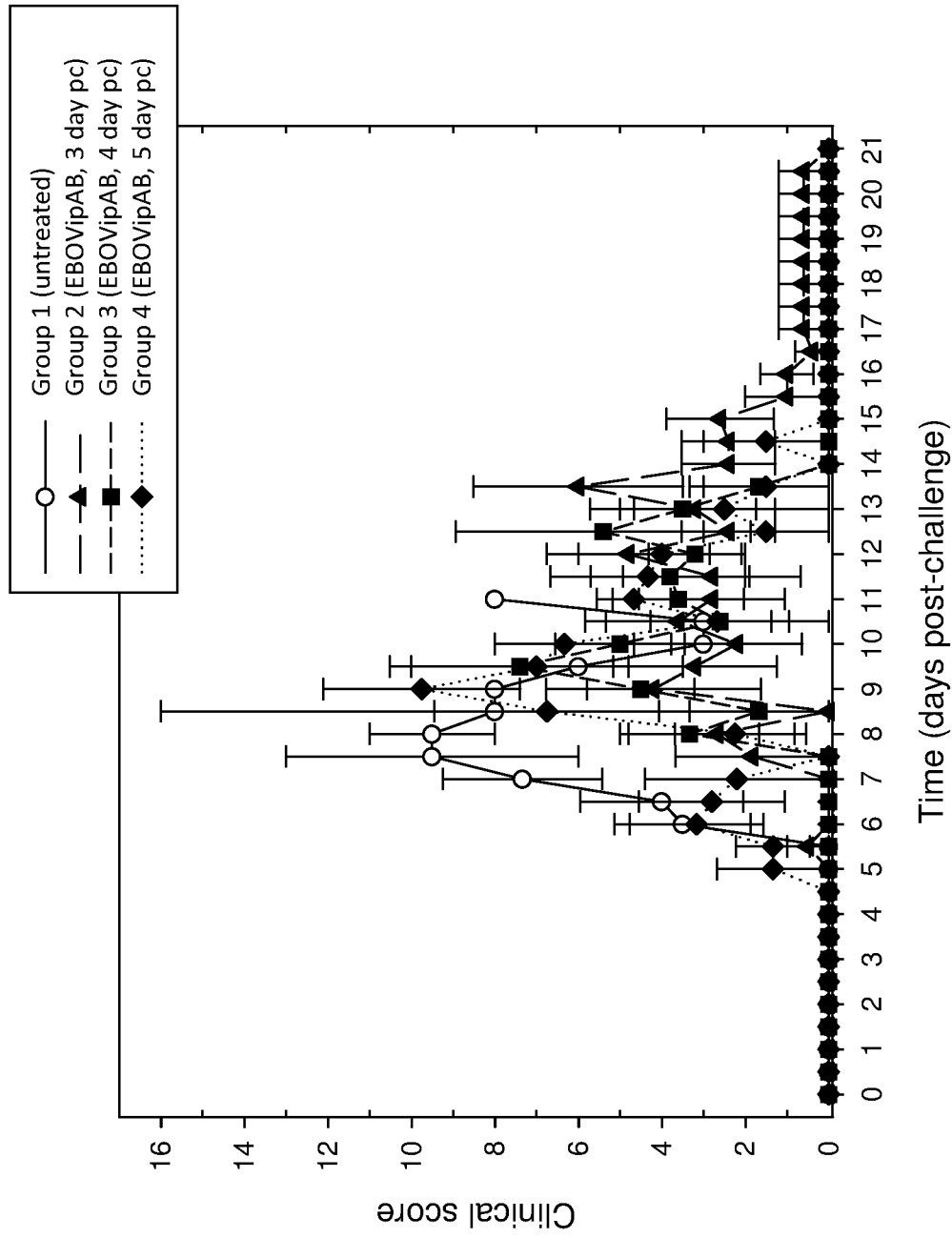

As shown in FIG. 12(B)-(D), Guinea pigs treated with EBOVIpAb showed a marked improvement over positive controls in terms of retained body weight (FIG. 12(B)), reduced change in body temperature (FIG. 12(C)), and reduced or delayed increase in clinical score (FIG. 12(D)). As noted above, this is particularly surprising in view of the high viral load at the time of EBOVIpAb administration.

These data confirm that patient outcome following EBOV infection may be drastically improved by the administration of EBOVIpAb.

Presence of EBOV RNA in the Peripheral Circulation.

Prior to the initial administration of EBOVIpAb on days 3, 4 or 5 post-challenge, blood was withdrawn from Guinea pigs and the presence of EBOV RNA detected by quantitative RT-PCR. Results indicated viremia in animals at day 3 post-challenge, which increased subsequently on day 4 and 5 post-challenge (FIG. 13).

Blood samples were collected at day 21 from the animals still viable at the scheduled end of the study, and whose intravenous catheters still allowed withdrawal of blood (EBOVIpAb given at days 3, 4 and 5 post-challenge, n=3, n=2 and n=2, respectively). Surprisingly, no viral RNA was detected in any of the blood samples collected at 21 days post-challenge, indicating that administration of EBOVIpAb had successfully cleared EBOV from the peripheral circulation.

Example 10 In Vivo Evaluation of EBOVIpAb Administered Post-challenge with EBOV (Non-human Primate Model)

Four groups of cynomolgus macaques (*Macaca fascicularis*) were tested. Groups 1-3 each consisted of four animals, and Group 4 consisted of 3 animals. Groups 1-3 were treated with 6 mL dose of EBOVIpAb (final concentration of 56.8 g/L) by intravenous infusion over a six minute period of a volume of 6 mL. Group 4 did not receive EBOVIpAb and served as an untreated control. All animals were challenged with a lethal dose of EBOV (corresponding to between 550 pfu and 220 pfu, by intramuscular administration). Groups 1-3 received five consecutive daily injections of EBOVIpAb, followed by alternating daily injections.

Group 1 received their first daily injection of EBOVIpAb one day after EBOV challenge, and thus received injections on D1-D5, D7, D9 and D11.

Group 2 received their first daily injection of EBOVIpAb two days after EBOV challenge, and thus received injections on D2-D6, D8, D10 and D12.

Group 3 received their first daily injection of EBOVIpAb three days after EBOV challenge, and thus received injections on D3-D7, D9, D11 and D13.

Mortality Analysis

As shown in FIG. 14, EBOV treatment of non-human primate controls (Group 4) proved fatal at ~day 6-10. Surprisingly, all of the non-human primates treated with EBOVIpAb at D1 (Group 1) survived challenge with EBOV, even at the endpoint of the experiment. Groups 2 and 3 also exhibited a marked improvement over Group 4 animals, both in terms of survival at the endpoint of the experiment (50% and 25% survival respectively), and also the onset of mortality within the respective groups (extending from 6 days in Group 4 to 10 days in Groups 2 and 3).

These advantageous results are particularly surprising in view of the highly stringent assay conditions, in which non-human primates were already infected with a lethal dose of EBOV prior to administration of EBOVIpAb.

Bodyweight Analysis

As shown in FIG. 15, EBOV treatment of non-human primate controls (Group 4) resulted in marked weight loss at 2-3 days post-challenge, which continued to decrease until mortality. Surprisingly, non-human primates treated with EBOVIpAb within one day of infection (Group 1) continued to gain weight until D2, followed by weight plateau until D3-D4, and then returning to a weight similar to D0. Groups 2 and 3 also exhibited a marked improvement in retained bodyweight, as compared to Group 4. These advantageous results are particularly surprising in view of the highly stringent assay conditions, in which non-human primates were already infected with a lethal dose of EBOV prior to administration of EBOVIpAb.

Similar to the Guinea pig data described above, these non-human primate data also confirm that patient outcome following EBOV infection may be drastically improved by the administration of EBOVIpAb.

Methods Section

Animals

Female Dunkin-Hartley guinea pigs were used for animal infection studies, with weights of 250 g to 350 g (Harlan Laboratories, UK). Before procedures involving the manipulation of animals, guinea pigs were anesthetised with 1.5% to 2% isofluorane in an induction change until full sedation was achieved. Animals infected with EBOV were housed within an isolator under climate-control conditions in an animal containment level 4 (CL4) room. Food and sterile water were available ad libitum. All procedures were undertaken according to the United Kingdom Animals (Scientific Procedures) Act 1986. A power calculation along with Fisher's exact test were performed using software G*Power ver.3.0.10 to determine group sizes for the experiments. A minimum group size of six met a power of 0.8 and alpha at 0.05. We also note that from previously published work in this area, that all animals become infected with EBOV at later passages. There were 10 guinea pigs depending on the group for each passage of the virus and a control group. From a practical standpoint of working at CL4 this number also represented the maximum number of animals that could be processed at the time. Of these animals, four were killed at day 7 post infection for preparation of virus and six to eight were carried on and used to measure clinical parameters. The study was performed under a UK Home Office Project License conforming to the Animal Procedures Act. Ethical review was performed by the Public Health England Animal Welfare and Ethical Review Board.

Virus

The EBOV Zaire ME718 strain was used in this work. This was originally isolated during an outbreak in October 1976 in Yambuku, Mongala Province in what is currently the northern Democratic Republic of the Congo, and it was simultaneously reported in three publications. Virus stocks used for this work were grown in VeroE6 cells (European Collection of Cell Cultures, UK) cultured in Leibovitz's L15 (L15) media containing 2% fetal calf serum (FCS), and aliquots were stored at −80° C. Virus titres were determined by 100-fold dilution with L15 media without any FCS added. A total of 100 µL of each dilution was overlaid onto semi-confluent cell monolayers in four replicate 12.5 cm$^2$ tissue culture flasks and left to absorb for 1 h. A volume of 5 mL media was then added and cells were incubated at 37° C. for 7 to 8 days. Cytopathic effects were determined by microscopy, and the results from each dilution were used to calculated 50% tissue culture infective dose (TCID$_{50}$) using the Reed-Muench method.

Animal Challenge

EBOV stock was diluted in sterile PBS to prepare the relevant dose of virus in a 0.2 mL volume. For passaging experiments (required for virus adaptation), the dose delivered was 10$^4$ TCID$_{50}$. Surplus inoculation was made to confirm concentration via back titration in cell culture. Guinea pigs were sedated, and subcutaneously inoculated with the virus suspension in the lower right quadrant of the back, then returned to their cages and monitored for adverse effects caused by the injection of the anaesthetic until the animals fully recovered. Negative control groups were injected with the same volume of PBS.

Observations and Monitoring

Animals were monitored at least twice daily, and observations (swelling at injection site, movement, breathing, food intake, water intake and appearance) recorded for the duration of the study. A set of humane clinical end points were defined (20% weight loss, or 10% weight loss and a clinical symptom) which indicated that the animal would be euthanised to prevent any unnecessary suffering. Weights of the animals were taken daily, and temperatures recorded using a pre-inserted temperature chip.

SEQ ID NOs:

Where an initial Met amino acid residue or a corresponding initial codon is indicated in any of the following SEQ ID NOs, said residue/codon is optional.

Ebola virus Mayinga Zaire glycoprotein
SEQ ID NO: 1
MGVTGILQLPRDRFKRTSFFLWVIILFQRTFSIPLGVIHNSTLQVSDVDK

LVCRDKLSSTNQLRSVGLNLEGNGVATDVPSATKRWGFRSGVPPKVVNYE

AGEWAENCYNLEIKKPDGSECLPAAPDGIRGFPRCRYVHKVSGTGPCAGD

FAFHKEGAFFLYDRLASTVIYRGTTFAEGVVAFLILPQAKKDFFSSHPLR

EPVNATEDPSSGYYSTTIRYQATGFGTNETEYLFEVDNLTYVQLESRFTP

QFLLQLNETIYTSGKRSNTTGKLIWKVNPEIDTTIGEWAFWETKKNLTRK

IRSEELSFTVVSNGAKNISGQSPARTSSDPGTNTTTEDHKIMASENSSAM

VQVHSQGREAAVSHLTTLATISTSPQSLTTKPGPDNSTHNTPVYKLDISE

ATQVEQHHRRTDNDSTASDTPSATTAAGPPKAENTNTSKSTDFLDPATTT

SPQNHSETAGNNNTHHQDTGEESASSGKLGLITNTIAGVAGLITGGRRTR

REAIVNAQPKCNPNLHYWTTQDEGAAIGLAWIPYFGPAAEGIYIEGLMHN

QDGLICGLRQLANETTQALQLFLRATTELRTFSILNRKAIDFLLQRWGGT

CHILGPDCCIEPHDWTKNITDKIDQIIHDFVDKTLPDQGDNDNWWTGWRQ

WIPAGIGVTGVIIAVIALFCICKFVF

Recombinant Ebola virus Mayinga Zaire glycoprotein, lacking Transmembrane Domain and membrane-proximal external region ("rGP")
SEQ ID NO: 2
MGVTGILQLPRDRFKRTSFFLWVIILFQRTFSIPLGVIHNSTLQVSDVDK

LVCRDKLSSTNQLRSVGLNLEGNGVATDVPSATKRWGFRSGVPPKVVNYE

AGEWAENCYNLEIKKPDGSECLPAAPDGIRGFPRCRYVHKVSGTGPCAGD

FAFHKEGAFFLYDRLASTVIYRGTTFAEGVVAFLILPQAKKDFFSSHPLR

EPVNATEDPSSGYYSTTIRYQATGFGTNETEYLFEVDNLTYVQLESRFTP

QFLLQLNETIYTSGKRSNTTGKLIWKVNPEIDTTIGEWAFWETKKNLTRK

IRSEELSFTVVSNGAKNISGQSPARTSSDPGTNTTTEDHKIMASENSSAM

VQVHSQGREAAVSHLTTLATISTSPQSLTTKPGPDNSTHNTPVYKLDISE

ATQVEQHHRRTDNDSTASDTPSATTAAGPPKAENTNTSKSTDFLDPATTT

SPQNHSETAGNNNTHHQDTGEESASSGKLGLITNTIAGVAGLITGGRRTR

REAIVNAQPKCNPNLHYWTTQDEGAAIGLAWIPYFGPAAEGIYIEGLMHN

QDGLICGLRQLANETTQALQLFLRATTELRTFSILNRKAIDFLLQRWGGT

CHILGPDCCIEPHDWTKNITDKIDQIIHDFVD

-continued
Nucleic acid encoding the polypeptide of SEQ ID NO: 1

SEQ ID NO: 3 atgggcgttacaggaatattgcagttacctcgtgatcgattcaagaggac atcattctttctttgggtaattatccttttccaaagaacattttccatcc cacttggagtcatccacaatagcacattacaggttagtgatgtcgacaaa ctagtttgtcgtgacaaactgtcatccacaaatcaattgagatcagttgg actgaatctcgaagggaatggagtggcaactgacgtgccatctgcaacta aaagatggggcttcaggtccggtgtcccaccaaaggtggtcaattatgaa gctggtgaatgggctgaaaactgctacaatcttgaaatcaaaaaacctga cgggagtgagtgtctaccagcagcgccagacgggattcggggcttccccc ggtgccggtatgtgcacaaagtatcaggaacgggaccgtgtgccggagac tttgccttccataaagagggtgctttcttcctgtatgatcgacttgcttc cacagttatctaccgaggaacgactttcgctgaaggtgtcgttgcatttc tgatactgccccaagctaagaaggacttcttcagctcacacccctt gaga gagccggtcaatgcaacgaggacccgtctagtggctactattctaccac aattagatatcaggctacaggttttggaaccaatgagacagagtacttgt tcgaggttgacaatttgacctacgtccaacttgaatcaagattcacacca cagtttctgctccagctgaatgagacaatatatacaagtgggaaaaggag caataccacgggaaaactaatttggaaggtcaaccccgaaattgatacaa caatcggggagtgggccttctgggaaactaaaaaaaacctcactagaaaa attcgcagtgaagagttgtctttcacagttgtatcaaacggagccaaaaa catcagtggtcagagtccggcgcgaacttcttccgacccagggaccaaca caacaactgaagaccacaaaatcatggcttcagaaaattcctctgcaatg gttcaagtgcacagtcaaggaagggaagctgcagtgtcgcatctaacaac ccttgccacaatctccacgagtccccaatccctcacaaccaaaccaggtc cggacaacagcacccataatacacccgtgtataaacttgacatctctgag gcaactcaagttgaacaacatcaccgcagaacagacaacgacagcacagc ctccgacactccctctgccacgaccgcagccggaccccaaaagcagaga acaccaacacgagcaagagcactgacttcctggaccccgccaccacaaca agtcccaaaaccacagcgagaccgctggcaacaacaacactcatcacca agataccggagaagagtgccagcagcgggaagctaggcttaattacca atactattgctggagtcgcaggactgatcacaggcgggagaagaactcga agagaagcaattgtcaatgctcaacccaaatgcaaccctaatttacatta ctggactactcaggatgaaggtgctgcaatcggactggcctggataccat atttcgggccagcagccgagggaatttacatagaggggctaatgcacaat caagatggtttaatctgtgggttgagacagctggccaacgagacgactca agctcttcaactgttcctgagagccacaactgagctacgcaccttttcaa tcctcaaccgtaaggcaattgatttcttgctgcagcgatggggcggcaca tgccacattctgggaccggactgctgtatcgaaccacatgattggaccaa gaacataacagacaaaattgatcagattattcatgattttgttgataaaa cccttccggaccaggggacaatgacaattggtggacaggatggagacaa -continued
tggataccggcaggtattggagttacaggcgttataattgcagttatcgc tttattctgtatatgcaaatttgtcttttag Nucleic acid encoding the polypeptide of SEQ ID NO: 2

SEQ ID NO: 4 atgggcgttacaggaatattgcagttacctcgtgatcgattcaagaggac atcattctttctttgggtaattatccttttccaaagaacattttccatcc cacttggagtcatccacaatagcacattacaggttagtgatgtcgacaaa ctagtttgtcgtgacaaactgtcatccacaaatcaattgagatcagttgg actgaatctcgaagggaatggagtggcaactgacgtgccatctgcaacta aaagatggggcttcaggtccggtgtcccaccaaaggtggtcaattatgaa gctggtgaatgggctgaaaactgctacaatcttgaaatcaaaaaacctga cgggagtgagtgtctaccagcagcgccagacgggattcggggcttccccc ggtgccggtatgtgcacaaagtatcaggaacgggaccgtgtgccggagac tttgccttccataaagagggtgctttcttcctgtatgatcgacttgcttc cacagttatctaccgaggaacgactttcgctgaaggtgtcgttgcatttc tgatactgccccaagctaagaaggacttcttcagctcacacccctt gaga gagccggtcaatgcaacgaggacccgtctagtggctactattctaccac aattagatatcaggctaccggttttggaaccaatgagacagagtacttgt tcgaggttgacaatttgacctacgtccaacttgaatcaagattcacacca cagtttctgctccagctgaatgagacaattatacaagtgggaaaaggagc aataccacgggaaaactaatttggaaggtcaaccccgaaattgatacaac aatcggggagtgggccttctgggaaactaaaaaaaacctcactagaaaaa ttcgcagtgaagagttgtctttcacagttgtatcaaacggagccaaaaac atcagtggtcagagtccggcgcgaacttcttccgacccagggaccaacac aacaactgaagaccacaaaatcatggcttcagaaaattcctctgcaatgg ttcaagtgcacagtcaaggaagggaagctgcagtgtcgcatctaacaacc cttgccacaatctccacgagtccccaatccctcacaaccaaaccaggtcc ggacaacagcacccataatacacccgtgtataaacttgacatctctgagg caactcaagttgaacaacatcaccgcagaacagacaacgacagcacagcc tccgacactccctctgccacgaccgcagccggaccccaaaagcagagaa caccaacacgagcaagagcactgacttcctggaccccgccaccacaacaa gtccccaaaaccacagcgagaccgctggcaacaacaacactcatcaccaa gataccggagaagagtgccagcagcgggaagctaggcttaattaccaa tactattgctggagtcgcaggactgatcacaggcgggagaagaactcgaa gagaagcaattgtcaatgctcaacccaaatgcaaccctaatttacattac tggactactcaggatgaaggtgctgcaatcggactggcctggataccata tttcgggccagcagccgagggaatttacatagaggggctaatgcacaatc aagatggtttaatctgtgggttgagacagctggccaacgagacgactcaa gctcttcaactgttcctgagagccacaactgagctacgcaccttttcaat cctcaaccgtaaggcaattgatttcttgctgcagcgatggggcggcacat -continued gccacattctgggaccggactgctgtatcgaaccacatgattggaccaag aacataacagacaaaattgatcagattattcatgattttgttgat

Optimised nucleic acid encoding the polypeptide of SEQ ID NO: 2

SEQ ID NO: 5 atgggcgttacaggaatattgcagttacctcgtgatcgattcaagaggac atcattctttctttgggtaattatccttttccaaagaacattttccatcc cacttggagtcatccacaatagcacattacaggttagtgatgtcgacaaa ctagtttgtcgtgacaaactgtcatccacaaatcaattgagatcagttgg actgaatctcgaagggaatggagtggcaactgacgtgccatctgcaacta aaagatgggcttcaggtccggtgtcccaccaaaggtggtcaattatgaa gctggtgaatgggctgaaaactgctacaatcttgaaatcaaaaaacctga cgggagtgagtgtctaccagcagcgccagacgggattcggggcttcccc ggtgccggtatgtgcacaaagtatcaggaacgggaccgtgtgccggagac tttgccttccataaagagggtgctttcttcctgtatgatcgacttgcttc cacagttatctaccgaggaacgactttcgctgaaggtgtcgttgcatttc tgatactgccccaagctaagaaggacttcttcagctcacacccccttgaga gagccggtcaatgcaacggaggacccgtctagtggctactattctaccac aattagatatcaggctaccggctttggaaccaatgagacagagtacttgt tcgaggttgacaatttgacctacgtccaacttgaatcaagattcaccaca cagtttctgctccagctgaatgagacaatatatacaagtgggaaaaggag caataccacgggaaaactaatttggaaggtcaaccccgaaattgatacaa caatcggggagtgggccttctgggaaactaaaaaaaaacctcactagaaaa attcgcagtgaagagttgtctttcacagttgtatcaaacggagccaaaaa catcagtggtcagagtccggcgcgaacttcttccgacccagggaccaaca caacaactgaagaccacaaaatcatggcttcagaaaattcctctgcaatg gttcaagtgcacagtcaaggaagggaagctgcagtgtcgcatctaacaac ccttgccacaatctccacgagtccccaatccctcacaaccaaaccaggtc cggacaacagcacccataatacacccgtgtataaacttgacatctctgag gcaactcaagttgaacaacatcaccgcagaacagacaacgacagcacagc ctccgacactccctctgccacgaccgcagccggaccccaaaagcagaga acaccaacacgagcaagagcactgacttcctggaccccgccaccacaaca agtccccaaaaccacagcgagaccgctggcaacaacaacactcatcacca agataccggagaagagagtgccagcagcgggaagctaggcttaattacca atactattgctggagtcgcaggactgatcacaggcgggagaagaactcga agagaagcaattgtcaatgctcaacccaaatgcaaccctaatttacatta ctggactactcaggatgaaggtgctgcaatcggactggcctggataccat atttcgggccagcagccgagggaatttacatagaggggctaatgcacaat caagatggtttaatctgtgggttgagacagctggccaacgagacgactca agctcttcaactgttcctgagagccacaactgagctacgcacctttttcaa tcctcaaccgtaaggcaattgatttcttgctgcagcgatggggcggcaca tgccacattctgggaccggactgctgtatcgaaccacatgattggaccaa gaacataacagacaaaattgatcagattattcatgattttgttgat

---

The invention claimed is:

1. A composition comprising ovine polyclonal antibodies in a form suitable for administration in treating, suppressing or preventing Ebola virus disease in a patient, wherein said antibodies bind to Ebola virus glycoprotein, wherein said ovine polyclonal antibodies are raised against a recombinant Ebola virus glycoprotein, and wherein said recombinant Ebola virus glycoprotein lacks the endogenous transmembrane domain.

2. The composition according to claim 1, wherein said composition comprises one or more additional therapeutics.

3. The composition according to claim 1, wherein said one or more additional therapeutics targets a different component of said Ebola virus from said antibody.

4. The composition according to claim 1, wherein said recombinant Ebola virus glycoprotein lacks the endogenous transmembrane domain and the endogenous membrane-proximal external region.

5. The composition according to claim 1, wherein the recombinant Ebola virus glycoprotein also lacks the endogenous signal peptide.

6. The composition according to claim 1, wherein the recombinant Ebola virus glycoprotein comprises or consists of an amino acid sequence having 70% or more identity to SEQ ID NO: 2 and comprises an epitope of SEQ ID NO: 2.

7. The composition according to claim 1, wherein the recombinant Ebola virus glycoprotein comprises a fragment of at least 7 consecutive amino acids of SEQ ID NO: 2, and comprises an epitope of SEQ ID NO: 2.

8. The composition according to claim 1, wherein the ovine polyclonal antibodies are produced by a method comprising:
 (i) administering to a sheep a recombinant Ebola virus glycoprotein, wherein said recombinant Ebola virus glycoprotein lacks the endogenous transmembrane domain,
 (ii) allowing sufficient time for the generation of antibodies in the sheep, and
 (iii) obtaining the antibodies from the sheep.

9. A method of treating, suppressing or preventing Ebola virus disease in a patient, said method comprising administering to a patient an antibody composition comprising ovine polyclonal antibodies, wherein said polyclonal antibodies bind to Ebola virus glycoprotein, and wherein said polyclonal antibodies do not substantially bind to the endogenous transmembrane domain of Ebola virus glycoprotein, and wherein said ovine polyclonal antibodies are raised against recombinant Ebola virus glycoprotein, wherein said recombinant Ebola virus glycoprotein lacks the endogenous transmembrane domain.

10. The method according to claim 9, wherein said treating, suppressing or preventing comprises intravenous administration of said composition to said patient, oral administration of said composition to said patient, intraperitoneal administration of said composition to said patient, or intramuscular administration of said composition to said patient.

11. The method according to claim 9, wherein said patient is a mammal.

12. The method according to claim 9, wherein said mammal is a human.

13. The method according to claim 9, wherein said treating or suppressing comprises administering the composition to the patient within 5 days of infection with Ebola virus, within 2 days of infection with Ebola virus, within 1 day of infection with Ebola virus, within 12 hours of infection with Ebola virus, or more than 5 days after infection with Ebola virus.

14. The method according to claim 9, wherein said preventing comprises administering the composition to the patient prior to infection with Ebola virus.

15. The method according to claim 9, wherein said treating, suppressing or preventing comprises administration of one or more additional therapeutics.

16. The method according to claim 9, wherein said one or more additional therapeutics targets a different component of said Ebola virus from said antibody.

17. The method according to claim 9, wherein said ovine polyclonal antibodies are raised against recombinant Ebola virus glycoprotein, wherein said recombinant Ebola virus glycoprotein lacks the endogenous transmembrane domain and the endogenous membrane-proximal external region.

18. The method according to claim 17, wherein the recombinant Ebola virus glycoprotein comprises or consists of an amino acid sequence having 70% or more identity to SEQ ID NO: 2 and comprises an epitope of SEQ ID NO: 2, or comprises a fragment of at least 7 consecutive amino acids of SEQ ID NO: 2, and comprises an epitope of SEQ ID NO: 2.

19. The method according to claim 17, wherein the ovine polyclonal antibodies are produced by a method comprising:
 (i) administering to a sheep the recombinant Ebola virus glycoprotein, wherein said recombinant Ebola virus glycoprotein lacks the endogenous transmembrane domain,
 (ii) allowing sufficient time for the generation of antibodies in the sheep, and
 (iii) obtaining the antibodies from the sheep.

* * * * *

SEQUENCE LISTING

<160> NUMBER OF SEQ IDS: 5

<210> SEQ ID NO 1
<211> LENGTH: 676
<212> TYPE: PRT
<213> ORGANISM: Ebola virus Mayinga Zaire

<400> SEQUENCE: 1

Met Gly Val Thr Gly Ile Leu Gln Leu Pro Arg Asp Arg Phe Lys Arg
1               5                   10                  15

Thr Ser Phe Phe Leu Trp Val Ile Ile Leu Phe Gln Arg Thr Phe Ser
            20                  25                  30

Ile Pro Leu Gly Val Ile His Asn Ser Thr Leu Gln Val Ser Asp Val
        35                  40                  45

Asp Lys Leu Val Cys Arg Asp Lys Leu Ser Ser Thr Asn Gln Leu Arg
    50                  55                  60

Ser Val Gly Leu Asn Leu Glu Gly Asn Gly Val Ala Thr Asp Val Pro
65                  70                  75                  80

Ser Ala Thr Lys Arg Trp Gly Phe Arg Ser Gly Val Pro Pro Lys Val
                85                  90                  95

Val Asn Tyr Glu Ala Gly Glu Trp Ala Glu Asn Cys Tyr Asn Leu Glu
            100                 105                 110

Ile Lys Lys Pro Asp Gly Ser Glu Cys Leu Pro Ala Ala Pro Asp Gly
        115                 120                 125

```
Ile Arg Gly Phe Pro Arg Cys Arg Tyr Val His Lys Val Ser Gly Thr
    130                 135                 140
Gly Pro Cys Ala Gly Asp Phe Ala Phe His Lys Glu Gly Ala Phe Phe
145                 150                 155                 160
Leu Tyr Asp Arg Leu Ala Ser Thr Val Ile Tyr Arg Gly Thr Thr Phe
                165                 170                 175
Ala Glu Gly Val Val Ala Phe Leu Ile Leu Pro Gln Ala Lys Lys Asp
            180                 185                 190
Phe Phe Ser Ser His Pro Leu Arg Glu Pro Val Asn Ala Thr Glu Asp
        195                 200                 205
Pro Ser Ser Gly Tyr Tyr Ser Thr Thr Ile Arg Tyr Gln Ala Thr Gly
210                 215                 220
Phe Gly Thr Asn Glu Thr Glu Tyr Leu Phe Glu Val Asp Asn Leu Thr
225                 230                 235                 240
Tyr Val Gln Leu Glu Ser Arg Phe Thr Pro Gln Phe Leu Leu Gln Leu
                245                 250                 255
Asn Glu Thr Ile Tyr Thr Ser Gly Lys Arg Ser Asn Thr Thr Gly Lys
            260                 265                 270
Leu Ile Trp Lys Val Asn Pro Glu Ile Asp Thr Thr Ile Gly Glu Trp
        275                 280                 285
Ala Phe Trp Glu Thr Lys Lys Asn Leu Thr Arg Lys Ile Arg Ser Glu
290                 295                 300
Glu Leu Ser Phe Thr Val Val Ser Asn Gly Ala Lys Asn Ile Ser Gly
305                 310                 315                 320
Gln Ser Pro Ala Arg Thr Ser Ser Asp Pro Gly Thr Asn Thr Thr Thr
                325                 330                 335
Glu Asp His Lys Ile Met Ala Ser Glu Asn Ser Ser Ala Met Val Gln
            340                 345                 350
Val His Ser Gln Gly Arg Glu Ala Ala Val Ser His Leu Thr Thr Leu
        355                 360                 365
Ala Thr Ile Ser Thr Ser Pro Gln Ser Leu Thr Thr Lys Pro Gly Pro
370                 375                 380
Asp Asn Ser Thr His Asn Thr Pro Val Tyr Lys Leu Asp Ile Ser Glu
385                 390                 395                 400
Ala Thr Gln Val Glu Gln His Arg Arg Thr Asp Asn Asp Ser Thr
                405                 410                 415
Ala Ser Asp Thr Pro Ser Ala Thr Thr Ala Ala Gly Pro Pro Lys Ala
            420                 425                 430
Glu Asn Thr Asn Thr Ser Lys Ser Thr Asp Phe Leu Asp Pro Ala Thr
        435                 440                 445
Thr Thr Ser Pro Gln Asn His Ser Glu Thr Ala Gly Asn Asn Asn Thr
450                 455                 460
His His Gln Asp Thr Gly Glu Glu Ser Ala Ser Ser Gly Lys Leu Gly
465                 470                 475                 480
Leu Ile Thr Asn Thr Ile Ala Gly Val Ala Gly Leu Ile Thr Gly Gly
                485                 490                 495
Arg Arg Thr Arg Arg Glu Ala Ile Val Asn Ala Gln Pro Lys Cys Asn
            500                 505                 510
Pro Asn Leu His Tyr Trp Thr Thr Gln Asp Glu Gly Ala Ala Ile Gly
        515                 520                 525
Leu Ala Trp Ile Pro Tyr Phe Gly Pro Ala Ala Glu Gly Ile Tyr Ile
530                 535                 540
Glu Gly Leu Met His Asn Gln Asp Gly Leu Ile Cys Gly Leu Arg Gln
```

```
545                 550                 555                 560
Leu Ala Asn Glu Thr Thr Gln Ala Leu Gln Leu Phe Leu Arg Ala Thr
                565                 570                 575

Thr Glu Leu Arg Thr Phe Ser Ile Leu Asn Arg Lys Ala Ile Asp Phe
                580                 585                 590

Leu Leu Gln Arg Trp Gly Gly Thr Cys His Ile Leu Gly Pro Asp Cys
                595                 600                 605

Cys Ile Glu Pro His Asp Trp Thr Lys Asn Ile Thr Asp Lys Ile Asp
            610                 615                 620

Gln Ile Ile His Asp Phe Val Asp Lys Thr Leu Pro Asp Gln Gly Asp
625                 630                 635                 640

Asn Asp Asn Trp Trp Thr Gly Trp Arg Gln Trp Ile Pro Ala Gly Ile
                645                 650                 655

Gly Val Thr Gly Val Ile Ile Ala Val Ile Ala Leu Phe Cys Ile Cys
            660                 665                 670

Lys Phe Val Phe
        675

<210> SEQ ID NO 2
<211> LENGTH: 632
<212> TYPE: PRT
<213> ORGANISM: Artificial sequence
<220> FEATURE:
<223> OTHER INFORMATION: Recombinant Ebola virus Mayinga Zaire
      glycoprotein

<400> SEQUENCE: 2

Met Gly Val Thr Gly Ile Leu Gln Leu Pro Arg Asp Arg Phe Lys Arg
1               5                   10                  15

Thr Ser Phe Phe Leu Trp Val Ile Ile Leu Phe Gln Arg Thr Phe Ser
                20                  25                  30

Ile Pro Leu Gly Val Ile His Asn Ser Thr Leu Gln Val Ser Asp Val
            35                  40                  45

Asp Lys Leu Val Cys Arg Asp Lys Leu Ser Ser Thr Asn Gln Leu Arg
        50                  55                  60

Ser Val Gly Leu Asn Leu Glu Gly Asn Gly Val Ala Thr Asp Val Pro
65                  70                  75                  80

Ser Ala Thr Lys Arg Trp Gly Phe Arg Ser Gly Val Pro Pro Lys Val
                85                  90                  95

Val Asn Tyr Glu Ala Gly Glu Trp Ala Glu Asn Cys Tyr Asn Leu Glu
                100                 105                 110

Ile Lys Lys Pro Asp Gly Ser Glu Cys Leu Pro Ala Ala Pro Asp Gly
            115                 120                 125

Ile Arg Gly Phe Pro Arg Cys Arg Tyr Val His Lys Val Ser Gly Thr
        130                 135                 140

Gly Pro Cys Ala Gly Asp Phe Ala Phe His Lys Glu Gly Ala Phe Phe
145                 150                 155                 160

Leu Tyr Asp Arg Leu Ala Ser Thr Val Ile Tyr Arg Gly Thr Thr Phe
                165                 170                 175

Ala Glu Gly Val Val Ala Phe Leu Ile Leu Pro Gln Ala Lys Lys Asp
                180                 185                 190

Phe Phe Ser Ser His Pro Leu Arg Glu Pro Val Asn Ala Thr Glu Asp
            195                 200                 205

Pro Ser Ser Gly Tyr Tyr Ser Thr Thr Ile Arg Tyr Gln Ala Thr Gly
        210                 215                 220
```

```
Phe Gly Thr Asn Glu Thr Glu Tyr Leu Phe Glu Val Asp Asn Leu Thr
225                 230                 235                 240

Tyr Val Gln Leu Glu Ser Arg Phe Thr Pro Gln Phe Leu Leu Gln Leu
            245                 250                 255

Asn Glu Thr Ile Tyr Thr Ser Gly Lys Arg Ser Asn Thr Thr Gly Lys
        260                 265                 270

Leu Ile Trp Lys Val Asn Pro Glu Ile Asp Thr Thr Ile Gly Glu Trp
    275                 280                 285

Ala Phe Trp Glu Thr Lys Lys Asn Leu Thr Arg Lys Ile Arg Ser Glu
290                 295                 300

Glu Leu Ser Phe Thr Val Val Ser Asn Gly Ala Lys Asn Ile Ser Gly
305                 310                 315                 320

Gln Ser Pro Ala Arg Thr Ser Ser Asp Pro Gly Thr Asn Thr Thr Thr
            325                 330                 335

Glu Asp His Lys Ile Met Ala Ser Glu Asn Ser Ser Ala Met Val Gln
                340                 345                 350

Val His Ser Gln Gly Arg Glu Ala Ala Val Ser His Leu Thr Thr Leu
        355                 360                 365

Ala Thr Ile Ser Thr Ser Pro Gln Ser Leu Thr Thr Lys Pro Gly Pro
370                 375                 380

Asp Asn Ser Thr His Asn Thr Pro Val Tyr Lys Leu Asp Ile Ser Glu
385                 390                 395                 400

Ala Thr Gln Val Glu Gln His His Arg Arg Thr Asp Asn Asp Ser Thr
            405                 410                 415

Ala Ser Asp Thr Pro Ser Ala Thr Thr Ala Ala Gly Pro Pro Lys Ala
        420                 425                 430

Glu Asn Thr Asn Thr Ser Lys Ser Thr Asp Phe Leu Asp Pro Ala Thr
    435                 440                 445

Thr Thr Ser Pro Gln Asn His Ser Glu Thr Ala Gly Asn Asn Asn Thr
450                 455                 460

His His Gln Asp Thr Gly Glu Glu Ser Ala Ser Ser Gly Lys Leu Gly
465                 470                 475                 480

Leu Ile Thr Asn Thr Ile Ala Gly Val Ala Gly Leu Ile Thr Gly Gly
            485                 490                 495

Arg Arg Thr Arg Arg Glu Ala Ile Val Asn Ala Gln Pro Lys Cys Asn
        500                 505                 510

Pro Asn Leu His Tyr Trp Thr Thr Gln Asp Glu Gly Ala Ala Ile Gly
    515                 520                 525

Leu Ala Trp Ile Pro Tyr Phe Gly Pro Ala Ala Glu Gly Ile Tyr Ile
530                 535                 540

Glu Gly Leu Met His Asn Gln Asp Gly Leu Ile Cys Gly Leu Arg Gln
545                 550                 555                 560

Leu Ala Asn Glu Thr Thr Gln Ala Leu Gln Leu Phe Leu Arg Ala Thr
            565                 570                 575

Thr Glu Leu Arg Thr Phe Ser Ile Leu Asn Arg Lys Ala Ile Asp Phe
        580                 585                 590

Leu Leu Gln Arg Trp Gly Gly Thr Cys His Ile Leu Gly Pro Asp Cys
    595                 600                 605

Cys Ile Glu Pro His Asp Trp Thr Lys Asn Ile Thr Asp Lys Ile Asp
610                 615                 620

Gln Ile Ile His Asp Phe Val Asp
625                 630
```

<210> SEQ ID NO 3
<211> LENGTH: 2031
<212> TYPE: DNA
<213> ORGANISM: Ebola virus Mayinga Zaire

<400> SEQUENCE: 3

```
atgggcgtta caggaatatt gcagttacct cgtgatcgat tcaagaggac atcattcttt      60
ctttgggtaa ttatcctttt ccaaagaaca ttttccatcc cacttggagt catccacaat     120
agcacattac aggttagtga tgtcgacaaa ctagtttgtc gtgacaaact gtcatccaca     180
aatcaattga gatcagttgg actgaatctc gaagggaatg gagtggcaac tgacgtgcca     240
tctgcaacta aagatggggg cttcaggtcc ggtgtcccac caaaggtggt caattatgaa     300
gctggtgaat gggctgaaaa ctgctacaat cttgaaatca aaaaacctga cgggagtgag     360
tgtctaccag cagcgccaga cgggattcgg gcttccccc ggtgccggta tgtgcacaaa     420
gtatcaggaa cgggaccgtg tgccggagac tttgccttcc ataaagaggg tgctttcttc     480
ctgtatgatc gacttgcttc cacagttatc taccgaggaa cgactttcgc tgaaggtgtc     540
gttgcatttc tgatactgcc ccaagctaag aaggacttct tcagctcaca ccccttgaga     600
gagccggtca atgcaacgga ggacccgtct agtggctact attctaccac aattagatat     660
caggctaccg gttttggaac aatgagaca gagtacttgt tcgaggttga caatttgacc     720
tacgtccaac ttgaatcaag attcaccaca cagtttctgc tccagctgaa tgagacaata     780
tatacaagtg ggaaaggag caataccacg ggaaaactaa tttggaaggt caaccccgaa     840
attgatacaa caatcgggga gtgggccttc tgggaaacta aaaaaaacct cactagaaaa     900
attcgcagtg aagagttgtc tttcacagtt gtatcaaacg gagccaaaaa catcagtggt     960
cagagtccgg cgcgaacttc ttccgaccca gggaccaaca caacaactga agaccacaaa    1020
atcatggctt cagaaaattc ctctgcaatg gttcaagtgc acagtcaagg aagggaagct    1080
gcagtgtcgc atctaacaac ccttgccaca atctccacga gtcccaatc cctcacaacc    1140
aaaccaggtc cggacaacag cacccataat acaccgtgt ataaacttga catctctgag    1200
gcaactcaag ttgaacaaca tcaccgcaga acagacaacg acagcacagc ctccgacact    1260
ccctctgcca cgaccgcagc cggacccccc aaagcagaga acaccaacac gagcaagagc    1320
actgacttcc tggaccccgc caccacaaca gtccccaaa accacagcga ccgctggc     1380
aacaacaaca ctcatcacca agatccggaa gagagagtg ccagcagcgg gaagctaggc    1440
ttaattacca atactattgc tggagtcgca ggactgatca caggcgggag aagaactcga    1500
agagaagcaa ttgtcaatgc tcaacccaaa tgcaaccccta atttacatta ctggactact    1560
caggatgaag gtgctgcaat cggactggcc tggataccat atttcgggcc agcagccgag    1620
ggaatttaca tagaggggct aatgcacaat caagatggtt taatctgtgg gttgagacag    1680
ctggccaacg agacgactca agctcttcaa ctgttcctga gagcacaacc tgagctacgc    1740
accttttcaa tcctcaaccg taaggcaatt gatttcttgc tgcagcgatg gggcggcaca    1800
tgccacattc tgggaccgga ctgctgtatc gaaccacatg attggaccaa gaacataaca    1860
gacaaaattg atcagattat tcatgatttt gttgataaaa cccttccgga ccaggggac    1920
aatgacaatt ggtggacagg atggagacaa tggataccgg caggtattgg agttacaggc    1980
gttataattg cagttatcgc tttattctgt atatgcaaat ttgtcttta g              2031
```

<210> SEQ ID NO 4
<211> LENGTH: 1896
<212> TYPE: DNA

<213> ORGANISM: Artificial sequence
<220> FEATURE:
<223> OTHER INFORMATION: Nucleic acid encoding SEQ ID NO: 2

<400> SEQUENCE: 4

```
atgggcgtta caggaatatt gcagttacct cgtgatcgat tcaagaggac atcattcttt      60
ctttgggtaa ttatccttt ccaaagaaca ttttccatcc cacttggagt catccacaat     120
agcacattac aggttagtga tgtcgacaaa ctagtttgtc gtgacaaact gtcatccaca     180
aatcaattga gatcagttgg actgaatctc gaagggaatg gagtggcaac tgacgtgcca     240
tctgcaacta aagatgggg cttcaggtcc ggtgtccac caaggtggt caattatgaa        300
gctggtgaat gggctgaaaa ctgctacaat cttgaaatca aaaaacctga cgggagtgag     360
tgtctaccag cagcgccaga cgggattcgg ggcttccccc ggtgccggta tgtgcacaaa     420
gtatcaggaa cgggaccgtg tgccggagac tttgccttcc ataaagaggg tgctttcttc     480
ctgtatgatc gacttgcttc cacagttatc taccgaggaa cgactttcgc tgaaggtgtc     540
gttgcatttc tgatactgcc ccaagctaag aaggacttct cagctcaca ccccttgaga       600
gagccggtca atgcaacgga ggacccgtct agtggctact attctaccac aattagatat     660
caggctaccg ttttggaac caatgagaca gagtacttgt tcgaggttga caatttgacc      720
tacgtccaac ttgaatcaag attcacacca cagtttctgc tccagctgaa tgagacaata    780
tatacaagtg gaaaaggag caataccacg ggaaaactaa tttggaaggt caaccccgaa      840
attgatacaa caatcgggga gtgggccttc tgggaaacta aaaaaaacct cactagaaaa    900
attcgcagtg aagagttgtc tttcacagtt gtatcaaacg gagccaaaaa catcagtggt     960
cagagtccgg cgcgaacttc ttccgaccca gggaccaaca caacaactga agaccacaaa    1020
atcatggctt cagaaaattc ctctgcaatg gttcaagtgc acagtcaagg aagggaagct    1080
gcagtgtcgc atctaacaac ccttgccaca atctccacga gtccccaatc cctcacaacc    1140
aaaccaggtc cggacaacag cacccataat acacccgtgt ataaacttga catctctgag    1200
gcaactcaag ttgaacaaca tcaccgcaga acagacaacg acagcacagc ctccgacact    1260
ccctctgcca cgaccgcagc cggaccccca aaagcagaga acaccaacac gagcaagagc    1320
actgacttcc tggaccccgc caccacaaca gtccccaaa ccacagcga ccgctggc         1380
aacaacaaca ctcatcacca agataccgga gaagagagtg ccagcagcgg gaagctaggc    1440
ttaattacca atactattgc tggagtcgca ggactgatca caggcgggag aagaactcga    1500
agagaagcaa ttgtcaatgc tcaacccaaa tgcaaccta atttacatta ctggactact    1560
caggatgaag gtgctgcaat cggactggcc tggataccat atttcgggcc agcagccgag    1620
ggaatttaca gagggggct aatgcacaat caagatggtt taatctgtgg gttgagacag    1680
ctggccaacg agacgactca agctcttcaa ctgttcctga gccacaac tgagctacgc       1740
acctttcaa tcctcaaccg taaggcaatt gatttcttgc tgcagcgatg gggcggcaca    1800
tgccacattc tgggaccgga ctgctgtatc gaaccacatg attggaccaa gaacataaca    1860
gacaaaattg atcagattat tcatgatttt gttgat                              1896
```

<210> SEQ ID NO 5
<211> LENGTH: 1896
<212> TYPE: DNA
<213> ORGANISM: Artificial sequence
<220> FEATURE:
<223> OTHER INFORMATION: Opimised nucleic acid encoding SEQ ID NO: 2

<400> SEQUENCE: 5

-continued

```
atgggcgtta caggaatatt gcagttacct cgtgatcgat tcaagaggac atcattcttt    60
ctttgggtaa ttatccttt ccaaagaaca ttttccatcc cacttggagt catccacaat    120
agcacattac aggttagtga tgtcgacaaa ctagtttgtc gtgacaaact gtcatccaca    180
aatcaattga gatcagttgg actgaatctc gaagggaatg gagtggcaac tgacgtgcca    240
tctgcaacta aaagatgggg cttcaggtcc ggtgtcccac caaaggtggt caattatgaa    300
gctggtgaat gggctgaaaa ctgctacaat cttgaaatca aaaaacctga cgggagtgag    360
tgtctaccag cagcgccaga cgggattcgg gcttccccc ggtgccggta tgtgcacaaa    420
gtatcaggaa cgggaccgtg tgccggagac tttgccttcc ataaagaggg tgctttcttc    480
ctgtatgatc gacttgcttc cacagttatc taccgaggaa cgactttcgc tgaaggtgtc    540
gttgcatttc tgatactgcc ccaagctaag aaggacttct tcagctcaca ccccttgaga    600
gagccggtca atgcaacgga ggacccgtct agtggctact attctaccac aattagatat    660
caggctaccg gctttggaac caatgagaca gagtacttgt tcgaggttga caatttgacc    720
tacgtccaac ttgaatcaag attcacacca cagtttctgc tccagctgaa tgagacaata    780
tatacaagtg ggaaaaggag caataccacg ggaaaactaa tttggaaggt caaccccgaa    840
attgatacaa caatcgggga gtgggccttc tgggaaacta aaaaaaacct cactagaaaa    900
attcgcagtg aagagttgtc tttcacagtt gtatcaaacg gagccaaaaa catcagtggt    960
cagagtccgg cgcgaacttc ttccgaccca gggaccaaca caacaactga agaccacaaa    1020
atcatggctt cagaaaattc ctctgcaatg gttcaagtgc acagtcaagg aagggaagct    1080
gcagtgtcgc atctaacaac ccttgccaca atctccacga gtccccaatc cctcacaacc    1140
aaaccaggtc cggacaacag cacccataat acacccgtgt ataaacttga catctctgag    1200
gcaactcaag ttgaacaaca tcaccgcaga acagacaacg acagcacagc ctccgacact    1260
ccctctgcca cgaccgcagc cggaccccca aaagcagaga acaccaacac gagcaagagc    1320
actgacttcc tggaccccgc caccacaaca agtccccaaa accacagcga gaccgctggc    1380
aacaacaaca ctcatcacca agataccgga gaagagagtg ccagcagcgg gaagctaggc    1440
ttaattacca atactattgc tggagtcgca ggactgatca caggcgggag aagaactcga    1500
agagaagcaa ttgtcaatgc tcaacccaaa tgcaacccta atttacatta ctggactact    1560
caggatgaag gtgctgcaat cggactggcc tggataccat atttcgggcc agcagccgag    1620
ggaatttaca tagaggggct aatgcacaat caagatggtt taatctgtgg gttgagacag    1680
ctggccaacg agacgactca agctcttcaa ctgttcctga gagccacaac tgagctacgc    1740
accttttcaa tcctcaaccg taaggcaatt gatttcttgc tgcagcgatg gggcggcaca    1800
tgccacattc tgggaccgga ctgctgtatc gaaccacatg attggaccaa gaacataaca    1860
gacaaaattg atcagattat tcatgatttt gttgat                                1896
```